US007316925B2

(12) United States Patent
Draghia-Akli et al.

(10) Patent No.: US 7,316,925 B2

(45) Date of Patent: Jan. 8, 2008

(54) CODON OPTIMIZED SYNTHETIC PLASMIDS

(75) Inventors: Ruxandra Draghia-Akli, Houston, TX (US); Ronald V. Abruzzese, The Woodlands, TX (US); Douglas R. Kern, The Woodlands, TX (US)

(73) Assignee: VGX Pharmaceuticals, Inc., Blue Bell, PA (US)

( * ) Notice: Subject to any disclaimer, the term of this patent is extended or adjusted under 35 U.S.C. 154(b) by 396 days.

(21) Appl. No.: 10/619,939

(22) Filed: Jul. 15, 2003

(65) Prior Publication Data

US 2004/0092009 A1 May 13, 2004

Related U.S. Application Data

(60) Provisional application No. 60/396,247, filed on Jul. 16, 2002.

(51) Int. Cl.

| | |
|---|---|
| ***C12N 15/85*** | (2006.01) |
| ***C07H 21/04*** | (2006.01) |
| *A61K 48/00* | (2006.01) |

(52) U.S. Cl. ................ 435/320.1; 536/23.5; 536/24.1; 514/44

(58) Field of Classification Search .................... None
See application file for complete search history.

(56) References Cited

U.S. PATENT DOCUMENTS

| | | | | |
|---|---|---|---|---|
| 5,061,690 | A | 10/1991 | Kann | |
| 5,134,120 | A | 7/1992 | Boyd | |
| 5,292,721 | A | 3/1994 | Boyd | |
| 5,756,264 | A | 5/1998 | Schwartz et al. | |
| 6,114,148 | A | 9/2000 | Seed | |
| 6,423,693 | B1 | 7/2002 | Schwartz et al. | |
| 6,551,996 | B1 | 4/2003 | Schwartz | |
| 6,924,365 | B1 * | 8/2005 | Miller et al. | 536/23.1 |

FOREIGN PATENT DOCUMENTS

| | | | |
|---|---|---|---|
| WO | WO 01/06988 | A2 * | 2/2001 |
| WO | WO 01/66149 | A2 | 9/2001 |
| WO | WO 02/061037 | A2 | 8/2002 |

OTHER PUBLICATIONS

Verma et al. (1997) Nature 389:239-242.*
Marshall (1995) Science 269:1050-1055.*
Orkin et al. (1995) Report and recommendations of the panel to assess the NIH investment in research on gene therapy, published online at http://www.nih.gov/news/panelrep.html.*
Eck et al. (1996) Goodman & Gilman's The Pharmacological Basis of Therapeutics, 9th Edition, Chapter 5, McGraw-Hill, NY.*
Ross et al. 1996 Human gene Therapy 7:1781-1790.*
Rubanyi (2001) Mol. Aspects Med. 22:113-142.*
Schwaab et al. (2001) Semin. Thromb. Hemost. 27:417-424.*
Rissanen et al. (2001) Eur. J. Clin. Invest. 31:651-666.*
MacColl et al. (1999) J. Endocinol. 162:1-9.*
Plasmid map for pBS, http://www.stratagene.com/vectors/maps/pdf/pbs.gif.*
Ahara, H. and Miyazaki, J. (1998). Gene transfer into muscle by electroporation in vivo. Nat. Biotechnol. 16, 867-870.
Baird, A., Wehrenberg, W. B., and Ling, N. (1986). Relative potencies of human, rat, bovine/caprine, porcine and ovine hypothalamic growth hormone-releasing factors to release growth hormone by the rat anterior pituitary in vitro. Neuroendocrinology 42, 273-276.
Bercu, B. B., Walker, R. F., (1997). Growth Hormone Secretagogues in Children With Altered Growth. Acta Paediatrica 86, 102-106.
Blethen, S. L. (1995). Complications of growth hormone therapy in children. Curr. Opin. Pediatr. 7, 466-471.
Blethen, S. L. and Rundle, A.C. (1996). Slipped capital femoral epiphysis in children treated with growth hormone. A summary of the National Cooperative Growth Study experience. Horm. Res. 46, 113-116.
Bohlen, P., Esch, F., Brazeau, P., Ling, N., and Guillemin, R. (1983). Isolation and characterization of the porcine hypothalamic growth hormone releasing factor. Biochem. Biophys. Res. Commun. 116, 726-734.
Bohlen, P., Wehrenberg,W. B., Esch, F., Ling, N., Brazeau, P., and Guillemin, R. (1984). Rat hypothalamic growth hormone-releasing factor: isolation, sequence analysis and total synthesis. Biochemical & Biophysical Research Communications 125, 1005-1012.
Brazeau, P., Bohlen, P., Esch, F., Ling, N., Wehrenberg,W. B., and Guillemin, R. (1984). Growth hormone-releasing factor from ovine and caprine hypothalamus: isolation, sequence analysis and total synthesis. Biochemical & Biophysical Research Communications 125, 606-614.
Burgert, T. S., Vuguin, P. M., DiMartino-Nardi, J., Attie, K. M., and Saenger, P. (2002). Assessing insulin resistance: application of a fasting glucose to insulin ratio in growth hormone-treated children. Horm. Res. 57, 37-42.
Carrel, A. L. and Allen, D. B. (2000). Effects of growth hormone on body composition and bone metabolism. Endocrine. 12, 163-172.
Corpas, E., Harman, S. M., and Blackman, M. R. (1993a). Human growth hormone and human aging. [Review]. Endocrine Reviews 14, 20-39.

(Continued)

*Primary Examiner*—Daniel M. Sullivan
(74) *Attorney, Agent, or Firm*—Pepper Hamilton LLP

(57) ABSTRACT

One aspect of the current invention is an optimized synthetic mammalian expression plasmid (e.g. pAV0201). This new plasmid comprise a therapeutic element, and a replication element. The therapeutic element of the new plasmid comprises a eukaryotic promoter; a 5' untranslated region ("UTR"); a codon-optimized-eukaryotic therapeutic gene sequence; and a poly adenylation signal. The therapeutic elements of this plasmid are operatively linked and located in a first operatively-linked arrangement. Additionally, the optimized synthetic mammalian expression plasmid comprises replication elements, wherein the replication elements are operatively linked and located in a second operatively-linked arrangement. The replication elements comprise a selectable marker gene promoter, a ribosomal binding site, and an origin of replication. The first-operatively-linked arrangement and the second-operatively-linked arrangement comprise a circular structure of the codon optimized synthetic mammalian expression plasmid.

2 Claims, 23 Drawing Sheets

OTHER PUBLICATIONS

Corpas, E., Harman, S. M., Pineyro, M. A., Roberson, R., and Blackman, M. R. (1993b). Continuous subcutaneous infusions of growth hormone (GH) releasing hormone 1-44 for 14 days increase GH and insulin-like growth factor-I levels in old men. Journal of Clinical Endocrinology & Metabolism 76, 134-138.
Cuttler, L. (1996). The regulation of growth hormone secretion. Endocrinol. Metab Clin. North Am. 25, 541-571.
Danko, I. and Wolff, J. A. (1994). Direct gene transfer into muscle. [Review]. Vaccine 12, 1499-1502.
Darquet, A. M., Cameron, B., Wils, P., Scherman, D., and Crouzet, J. (1997). A new DNA vehicle for nonviral gene delivery: supercoiled minicircle. Gene Ther. 4, 1341-1349.
Darquet, A. M., Rangara, R., Kreiss, P., Schwartz, B., Naimi, S., Delaere, P., Crouzet, J., and Scherman, D. (1999). Minicircle: an improved DNA molecule for in vitro and in vivo gene transfer. Gene Ther. 6, 209-218.
Draghia-Akli, R., Fiorotto, M. L., Hill, L. A., Malone, P. B., Deaver, D. R., and Schwartz, R. J. (1999). Myogenic expression of an injectable protease-resistance growth hormone-releasing hormone augments long-term growth in pigs. Nat. Biotechnol. 17, 1179-1183.
Draghia-Akli, R., Li, X. G., Schwartz, R. J. (1997). Enhanced Growth By Ectopic Expression Of Growth Hormone Releasing Hormone Using An Injectable Myogenic Vector. nature biotechnology 15, 1285-1289.
Draghia-Akli, R., Malone, P. B., Hill, L. A., Ellis, K. M., Schwartz, R. J., and Nordstrom, J. L. (2002). Enhanced animal growth via ligand-regulated GHRH myogenic-injectable vectors. FASEB J. 16, 426-428.
Duck, S. C., et al., (1992). Subcutaneous growth hormone-releasing hormone therapy in growth hormone-deficient children: first year of therapy. Journal of Clinical Endocrinology & Metabolism 75, 1115-1120.
Esch, F., Bohlen, P., Ling, N., Brazeau, P., and Guillemin, R. (1983). Isolation and characterization of the bovine hypothalamic growth hormone releasing factor. Biochemical & Biophysical Research Communications 117, 772-779.
Evans, W. S., Vance, M. L. et al., (1985). Effects of intravenous, subcutaneous, and intranasal administration of growth hormone (GH)-releasing hormone-40 on serum GH concentrations in normal men. Journal of Clinical Endocrinology & Metabolism 61, 846-850.
Faglia, G., Arosio, M., and Bazzoni, N. (1992). Ectopic acromegaly. [Review]. Endocrinology & Metabolism Clinics of North America 21, 575-595.
Frohman, L. A., Downs, T. R., and Chomczynski, P. (1992). Regulation of growth hormone secretion. [Review]. Frontiers in Neuroendocrinology 13, 344-405.
Frohman, L. A., Downs, T. R., Heimer, E. P., and Felix, A. M. (1989a). Dipeptidylpeptidase IV and trypsin-like enzymatic degradation of human growth hormone-releasing hormone in plasma. J. Clin. Invest. 83, 1533-1540.
Frohman, L. A., Downs, T. R., Williams, T. C., Heimer,E.P., Pan,Y.C., and Felix,A.M. (1986). Rapid enzymatic degradation of growth hormone-releasing hormone by plasma in vitro and in vivo to a biologically inactive product cleaved at the NH2 terminus. J. Clin. Invest. 78, 906-913.
Geffner, M. (1997). Effects of growth hormone and insulin-like growth factor I. Acta Paediatr. Suppl 423, 76-79.
Hart, D. W., Herndon, D. N., Klein, G., Lee, S. B., Celis, M., Mohan, S., Chinkes, D. L., and Wolf, S. E. (2001). Attenuation of posttraumatic muscle catabolism and osteopenia by long-term growth hormone therapy. Ann. Surg. 233, 827-834.
Kotzmann, H., Yilmaz, N., Lercher, P., Riedl, M., Schmidt, A., Schuster, E., Kreuzer, S., Geyer, G., Frisch, H., Hori,W. H., Mayer, G., and Luger, A. (2001). Differential effects of growth hormone therapy in malnourished hemodialysis patients. Kidney Int. 60, 1578-1585.
Lal, S. O., Wolf, S. E., and Herndon, D. N. (2000). Growth hormone, burns and tissue healing. Growth Horm. IGF. Res. 10 Suppl B:S39-43., S39-43.
LeRoith, D., Yanowski, J., Kaldjian, E. P., Jaffe, E. S., LeRoith, T., Purdue, K., Cooper, B. D., Pyle, R., and Adler, W. (1996). The effects of growth hormone and insulin-like growth factor I on the immune system of aged female monkeys. Endocrinology 137, 1071-1079.
Lesbordes, J. C., Bordet, T., Haase, G., Castelnau-Ptakhine, L., Rouhani, S., Gilgenkrantz, H., and Kahn, A. (2002). In vivo electrotransfer of the cardiotrophin-1 gene into skeletal muscle slows down progression of motor neuron degeneration in pmn mice. Hum. Mol. Genet. 11, 1615-1625.
Manders, P. and Thomas, R. (2000). Immunology of DNA vaccines: CpG motifs and antigen presentation. Inflamm. Res. 49, 199-205.
Mayo, K. E., Cerelli, G. M., Rosenfeld, M. G., and Evans, R. M. (1985). Characterization of cDNA and genomic clones encoding the precursor to rat hypothalamic growth hormone-releasing factor. Nature 314, 464-467.
McCluskie, M. J., Weeratna, R. D., and Davis, H. L. (2000). The role of CpG in DNA vaccines. Springer Semin. Immunopathol. 22, 125-132.
McRory, J. E., Parker, R. L., and Sherwood,N.M. (1997). Expression and alternative processing of a chicken gene encoding both growth hormone-releasing hormone and pituitary adenylate cyclase-activating polypeptide. DNA Cell Biol. 16, 95-102.
Melmed, S. (1991). Extrapituitary Acromegaly. [Review]. Endocrinology & Metabolism Clinics of North America 20, 507-518.
Mulligan, K., Tai, V. W., and Schambelan, M. (1999). Use of growth hormone and other anabolic agents in AIDS wasting. JPEN J. Parenter. Enteral Nutr. 23, S202-S209.
Narum, D. L., Kumar, S., Roger, W. O., Fuhrmann, S. R., Liang, H., Oakley, M., Taye, A., Sim, B. K., and Hoffman, S. L. (2001). Codon optimization of gene fragments encoding *Plasmodium falciparum* merzoite proteins enhances DNA vaccine protein expression and immunogenicity in mice. Infect. Immun. 69, 7250-7253.
Scheule, R. K. (2000). The role of CpG motifs in immunostimulation and gene therapy. Adv. Drug Deliv. Rev. 44, 119-134.
Shi, H., Yan, P. S., Chen, C. M., Rahmatpanah, F., Lofton-Day, C., Caldwell, C. W., and Huang, T. H. (2002). Expressed CpG island sequence tag microarray for dual screening of DNA hypermethylation and gene silencing in cancer cells. Cancer Res. 62, 3214-3220.
Shiraishi, M., Sekiguchi, A., Terry, M. J., Oates, A. J., Miyamoto, Y., Chuu, Y. H., Munakata, M., and Sekiya, T. (2002). A comprehensive catalog of CpG islands methylated in human lung adenocarcinomas for the identification of tumor suppressor genes. Oncogene 21, 3804-3813.
Soubrier, F., Cameron, B., Manse, B., Somarriba, S., Dubertret, C., Jaslin, G., Jung, G., Caer, C. L., Dang, D., Mouvault, J. M., Scherman, D., Mayaux, J. F., and Crouzet, J. (1999). pCOR: a new design of plasmid vectors for nonviral gene therapy. Gene Ther. 6, 1482-1488.
Wolff, J. A., Ludtke, J. J., Acsadi, G., Williams, P., and Jani, A. (1992). Long-term persistence of plasmid DNA and foreign gene expression in mouse muscle. Human Molecular Genetics 1, 363-369.
Hamdan FF, Mousa A, Ribeiro P. Codon optimization improves heterologous expression of a *Schistosoma mansoni* cDNA in HEK293 cells. Parasitol Res. Jun. 2002;88(6):583-6. Epub Feb. 16, 2002.
Kim CH, Oh Y, Lee TH. Codon optimization for high-level expression of human erythropoietin (EPO) in mammalian cells. Gene: An International Journal on Genes and Genomes. Elsevier. Amsterdam, NL. Oct. 15, 1997;199(1-2):293-301.
Yew NS, Wysokenski DM, Wang KX, Ziegler RJ, Marshall J, McNeilly D, Cherry M, Osburn W, Cheng SH. Optimization of plasmid vectors for high-level expression in lung epithelial cells. Hum Gene Ther. Mar. 20, 1997;8(5):575-84.
Supplementary European Search Report Under Article 157(2)(a) EPC, from the European Patent Office, dated Oct. 10, 2006.

* cited by examiner

```
      M  I  E  Q   D  G  L   H  A  G   S  P  A  A   W  V  E   R  L  F   G  Y  D  W   A  Q  Q   T  I  G   C  S  D  A·
1     ATGATTGAAC AAGATGGATT GCACGCAGGT TCTCCGGCCG CTTGGGTGGA GAGGCTATTC GGCTATGACT GGGCACAACA GACAATCGGC TGCTCTGATG
      TACTAACTTG TTCTACCTAA CGTGCGTCCA AGAGGCCGGC GAACCCACCT CTCCGATAAG CCGATACTGA CCCGTGTTGT CTGTTAGCCG ACGAGACTAC
      · A  V  F   R  L  S   A  Q  G  R   P  V  L   F  V  K   T  D  L  S   G  A  L   N  E  L   Q  D  E  A   A  R  L·
101   CCGCCGTGTT CCGGCTGTCA GCGCAGGGGC GCCCGGTTCT TTTTGTCAAG ACCGACCTGT CCGGTGCCCT GAATGAACTG CAGGACGAGG CAGCGCGGCT
      GGCGGCACAA GGCCGACAGT CGCGTCCCCG CGGGCCAAGA AAAACAGTTC TGGCTGGACA GGCCACGGGA CTTACTTGAC GTCCTGCTCC GTCGCGCCGA
      ·S  W  L   A  T  T  G   V  P  C   A  A  V   L  D  V  V   T  E  A   G  R  D   W  L  L  L   G  E  V   P  G  Q
201   ATCGTGGCTG GCCACGACGG GCGTTCCTTG CGCAGCTGTG CTCGACGTTG TCACTGAAGC GGGAAGGGAC TGGCTGCTAT TGGGCGAAGT GCCGGGGCAG
      TAGCACCGAC CGGTGCTGCC CGCAAGGAAC GCGTCGACAC GAGCTGCAAC AGTGACTTCG CCCTTCCCTG ACCGACGATA ACCCGCTTCA CGGCCCCGTC
      D  L  L  S   S  H  L   A  P  A   E  K  V  S   I  M  A   D  A  M   R  R  L  H   T  L  D   P  A  T   C  P  F  D·
301   GATCTCCTGT CATCTCACCT TGCTCCTGCC GAGAAAGTAT CCATCATGGC TGATGCAATG CGGCGGCTGC ATACGCTTGA TCCGGCTACC TGCCCATTCG
      CTAGAGGACA GTAGAGTGGA ACGAGGACGG CTCTTTCATA GGTAGTACCG ACTACGTTAC GCCGCCGACG TATGCGAACT AGGCCGATGG ACGGGTAAGC
      · H  Q  A   K  H  R   I  E  R  A   R  T  R   M  E  A   G  L  V  D   Q  D  D   L  D  E   E  H  Q  G   L  A  P·
401   ACCACCAAGC GAAACATCGC ATCGAGCGAG CACGTACTCG GATGGAAGCC GGTCTTGTCG ATCAGGATGA TCTGGACGAA GAGCATCAGG GGCTCGCGCC
      TGGTGGTTCG CTTTGTAGCG TAGCTCGCTC GTGCATGAGC CTACCTTCGG CCAGAACAGC TAGTCCTACT AGACCTGCTT CTCGTAGTCC CCGAGCGCGG
      ·A  E  L   F  A  R  L   K  A  R   M  P  D   G  E  D  L   V  V  T   H  G  D   A  C  L  P   N  I  M   V  E  N
501   AGCCGAACTG TTCGCCAGGC TCAAGGCGCG CATGCCCGAC GGCGAGGATC TCGTCGTGAC TCATGGCGAT GCCTGCTTGC CGAATATCAT GGTGGAAAAT
      TCGGCTTGAC AAGCGGTCCG AGTTCCGCGC GTACGGGCTG CCGCTCCTAG AGCAGCACTG AGTACCGCTA CGGACGAACG GCTTATAGTA CCACCTTTTA
      G  R  F  S   G  F  I   D  C  G   R  L  G  V   A  D  R   Y  Q  D   I  A  L  A   T  R  D   I  A  E   E  L  G  G·
601   GGCCGCTTTT CTGGATTCAT CGACTGTGGC CGGCTGGGTG TGGCGGACCG CTATCAGGAC ATAGCGTTGG CTACCCGTGA TATTGCTGAA GAGCTTGGCG
      CCGGCGAAAA GACCTAAGTA GCTGACACCG GCCGACCCAC ACCGCCTGGC GATAGTCCTG TATCGCAACC GATGGGCACT ATAACGACTT CTCGAACCGC
      · E  W  A   D  R  F   L  V  L  Y   G  I  A   A  P  D   S  Q  R  I   A  F  Y   R  L  L   D  E  F  F   *
701   GCGAATGGGC TGACCGCTTC CTCGTGCTTT ACGGTATCGC CGCTCCCGAT TCGCAGCGCA TCGCCTTCTA TCGCCTTCTT GACGAGTTCT TCTGA
      CGCTTACCCG ACTGGCGAAG GAGCACGAAA TGCCATAGCG GCGAGGGCTA AGCGTCGCGT AGCGGAAGAT AGCGGAAGAA CTGCTCAAGA AGACT
```

Figure 3

```
 +3  A  M  V   L  W  V  L   F  V  I   L  I  L   T  S  G  S   H  C  S   L  P  P   S  P  P  F   R  M  Q   R  H  V
  1 GCCATGGTGC TCTGGGTGCT CTTTGTGATC CTCATCCTCA CCAGCGGCAG CCACTGCAGC CTGCCTCCCA GCCCTCCCTT CAGGATGCAG AGGCACGTGG
    CGGTACCACG AGACCCACGA GAAACACTAG GAGTAGGAGT GGTCGCCGTC GGTGACGTCG GACGGAGGGT CGGGAGGGAA GTCCTACGTC TCCGTGCACC

 +3 D  A  I  F   T  T  N   Y  R  K   L  L  S  Q   L  Y  A   R  K  V   I  Q  D  I   M  N  K   Q  G  E   R  I  Q  E
101 ACGCCATCTT CACCACCAAC TACAGGAAGC TGCTGAGCCA GCTGTACGCC AGGAAGGTGA TCCAGGACAT CATGAACAAG CAGGGCGAGA GGATCCAGGA
    TGCGGTAGAA GTGGTGGTTG ATGTCCTTCG ACGACTCGGT CGACATGCGG TCCTTCCACT AGGTCCTGTA GTACTTGTTC GTCCCGCTCT CCTAGGTCCT

 +3  Q  R  A   R  L  S   &  #  A  C
201 GCAGAGGGCC AGGCTGAGCT GATAAGCTTG C
    CGTCTCCCGG TCCGACTCGA CTATTCGAAC G
```

Figure 5

```
GHRH-m Ori  .CCATGGTGCTCTGGGTGCTCTTTGTGATCCTCATCCTCACCAGTGGCTCCCACTGCTCA   60
             |||||||||||||||||||||||||||||||||||||||||||| |||  |||||||
GHRH-m Opt  GCCATGGTGCTCTGGGTGCTCTTTGTGATCCTCATCCTCACCAGCGGCAGCCACTGCAGC

GHRH-m Ori  CTGCCCCCTCACCTCCCTTCAGGATGCAGCGACACGTGGACGCCATCTTCACCACCAAC  120
            ||||| |||   ||||||||||||||||| | |||||||||||||||||||||||||||
GHRH-m Opt  CTGCCTCCCAGCCCTCCCTTCAGGATGCAGAGGCACGTGGACGCCATCTTCACCACCAAC

GHRH-m Ori  TACAGGAAGCTGCTGAGCCAGCTGTACGCCAGGAAGGTGATCCAGGACATCATGAACAAG  180
            ||||||||||||||||||||||||||||||||||||||||||||||||||||||||||||
GHRH-m Opt  TACAGGAAGCTGCTGAGCCAGCTGTACGCCAGGAAGGTGATCCAGGACATCATGAACAAG

GHRH-m Ori  CAGGGCGAGAGAATCCAGGAGCAGAGGGCCAGGCTGAGCTGATAAGCTT..  231
            ||||||||||| |||||||||||||||||||||||||||||||||||||
GHRH-m Opt  CAGGGCGAGAGGATCCAGGAGCAGAGGGCCAGGCTGAGCTGATAAGCTTGC
```

Figure 6

```
GHRH-M Ori  .MVLWVLFVILILTSGSHCSLPPSPPFRMQRHVDAIFTTNYRKLLSQLYARKVIQDIMNK  60
             |||||||||||||||||||||||||||||||||||||||||||||||||||||||||||
GHRH-M opti AMVLWVLFVILILTSGSHCSLPPSPPFRMQRHVDAIFTTNYRKLLSQLYARKVIQDIMNK

GHRH-M Ori  QGERIQEQRARLSA.  75
            ||||||||||||||
GHRH-M opti QGERIQEQRARLSAC
```

Figure 7

```
 +3  A  M  A   L  W  V  F   F  V  L   L  T  L   T  S  G  S   H  C  S   L  P  P   S  P  P  F   R  V  R   R  H  A
   1 GCCATGGCCC TGTGGGTGTT CTTCGTGCTG CTGACCCTGA CCAGCGGAAG CCACTGCAGC CTGCCTCCCA GCCCTCCCTT CAGGGTGCGC CGGCACGCCG
     CGGTACCGGG ACACCCACAA GAAGCACGAC GACTGGGACT GGTCGCCTTC GGTGACGTCG GACGGAGGGT CGGGAGGGAA GTCCCACGCG GCCGTGCGGC

 +3 D  A  I  F   T  S  S  Y  R  R   I  L  G  Q   L  Y  A   R  K  L   L  H  E  I   M  N  R   Q  Q  G   E  R  N  Q
 101 ACGCCATCTT CACCAGCAGC TACAGGAGGA TCCTGGGCCA GCTGTACGCT AGGAAGCTCC TGCACGAGAT CATGAACAGG CAGCAGGGCG AGAGGAACCA
     TGCGGTAGAA GTGGTCGTCG ATGTCCTCCT AGGACCCGGT CGACATGCGA TCCTTCGAGG ACGTGCTCTA GTACTTGTCC GTCGTCCCGC TCTCCTTGGT

 +3   E  Q  R   S  R  F   N  &  #  A   C
 201 GGAGCAGAGG AGCAGGTTCA ACTGATAAGC TTGC
     CCTCGTCTCC TCGTCCAAGT TGACTATTCG AACG
```

Figure 9

```
 GHRH-R Ori  GCCATGGCACTCTGGGTGTTCTTTGTGCTCCTCACCCTCACCAGTGGCTCCCACTGCTCA   60
             |||||||| || ||||||||||| ||||| || ||||| ||||| ||   |||||||
GHRH-R opti  GCCATGGCCCTGTGGGTGTTCTTCGTGCTGCTGACCCTGACCAGCGGAAGCCACTGCAGC

 GHRH-R Ori  CTGCCCCCCTCACCTCCCTTCAGGGTGCGGCGGCACGCCGACGCCATCTTCACCAGCAGC  120
             ||||| |||   ||||||||||||||||| ||||||||||||||||||||||||||||||
GHRH-R opti  CTGCCTCCCAGCCCTCCCTTCAGGGTGCGCCGGCACGCCGACGCCATCTTCACCAGCAGC

 GHRH-R Ori  TACAGGAGAATCCTGGGCCAGCTGTACGCCAGGAAACTGCTGCACGAGATCATGAACAGG  180
             |||||||| |||||||||||||||||||| ||||| || |||||||||||||||||||||
GHRH-R opti  TACAGGAGGATCCTGGGCCAGCTGTACGCTAGGAAGCTCCTGCACGAGATCATGAACAGG

 GHRH-R Ori  CAGCAGGGCGAGAGGAACCAGGAGCAGAGGTCCAGGTTCAACTGATAAGCTTGC  234
             ||||||||||||||||||||||||||||||  ||||||||||||||||||||||
GHRH-R opti  CAGCAGGGCGAGAGGAACCAGGAGCAGAGGAGCAGGTTCAACTGATAAGCTTGC
```

Figure 10

```
 GHRH-R Ori  .MALWVFFVLLTLTSGSHCSLPPSPPFRVRRHADAIFTSSYRRILGQLYARKLLHEIMNR   60
              |||||||||||||||||||||||||||||||||||||||||||||||||||||||||||
GHRH-R opti  AMALWVFFVLLTLTSGSHCSLPPSPPFRVRRHADAIFTSSYRRILGQLYARKLLHEIMNR

 GHRH-R Ori  QQGERNQEQRSRFNA.   76
             |||||||||||||||
GHRH-R opti  QQGERNQEQRSRFNAC
```

Figure 11

```
 +3  A  M  V   L  W  V  F   F  L  V   T  L  T   L  S  S  G   S  H  G   S  L  P   S  Q  P  L   R  I  P   R  Y  A
  1 GCCATGGTGC TGTGGGTGTT CTTCCTGGTG ACCCTGACCC TGAGCAGCGG CTCCCACGGC TCCCTGCCCT CCCAGCCTCT GCGCATCCCT CGCTACGCCG
    CGGTACCACG ACACCCACAA GAAGGACCAC TGGGACTGGG ACTCGTCGCC GAGGGTGCCG AGGGACGGGA GGGTCGGAGA CGCGTAGGGA GCGATGCGGC

 +3 D  A  I  F   T  N  S   Y  R  K   V  L  G  Q   L  S  A   R  K  L   L  Q  D  I   M  N  R   Q  Q  G   E  R  N  Q
101 ACGCCATCTT CACCAACAGC TACCGCAAGG TGCTCGGCCA GCTCAGCGCC CGCAAGCTCC TGCAGGACAT CATGAACCGG CAGCAGGGCG AGCGCAACCA
    TGCGGTAGAA GTGGTTGTCG ATGGCGTTCC ACGAGCCGGT CGAGTCGCGG GCGTTCGAGG ACGTCCTGTA GTACTTGGCC GTCGTCCCGC TCGCGTTGGT

 +3   E  Q  G   A  &  #   A  C
201 GGAGCAGGGA GCCTGATAAG CTTGC
    CCTCGTCCCT CGGACTATTC GAACG
```

Figure 13

```
GHRH-B Ori  .CCATGGTGCTCTGGGTGTTCTTCCTCGTGACCCTCACCCTCAGCAGCGGCTCCCACGGT   60
             |||||||||| |||||||||||||| |||||||| ||||| ||||||||||||||||| 
GHRH-B opti GCCATGGTGCTGTGGGTGTTCTTCCTGGTGACCCTGACCCTGAGCAGCGGCTCCCACGGC

GHRH-B Ori  TCCCTGCCTTCCCAGCCTCTCAGGATTCCACGGTACGCCGACGCCATCTTCACCAACAGC  120
            |||||||| |||||||||||  | || || || |||||||||||||||||||||||||||
GHRH-B opti TCCCTGCCCTCCCAGCCTCTGCGCATCCCTCGCTACGCCGACGCCATCTTCACCAACAGC

GHRH-B Ori  TACCGGAAGGTGCTGGGCCAGCTGTCCGCCCGGAAGCTGCTGCAGGACATCATGAACAGG  180
            ||||| |||||||| ||||||||   |||||| ||||| |||||||||||||||||| ||
GHRH-B opti TACCGCAAGGTGCTCGGCCAGCTCAGCGCCCGCAAGCTCCTGCAGGACATCATGAACCGG

GHRH-B Ori  CAGCAGGGCGAGAGAAACCAGGAGCAGGGCGCCTGATAAGCTT..  225
            |||||||||||| | |||||||||||||| |||||||||||||
GHRH-B opti CAGCAGGGCGAGCGCAACCAGGAGCAGGGAGCCTGATAAGCTTGC
```

Figure 14

```
 GHRH-B Ori .MVLWVFFLVTLTLSSGSHGSLPSQPLRIPRYADAIFTNSYRKVLGQLSARKLLQDIMNR  60
             |||||||||||||||||||||||||||||||||||||||||||||||||||||||||||
GHRH-B opti AMVLWVFFLVTLTLSSGSHGSLPSQPLRIPRYADAIFTNSYRKVLGQLSARKLLQDIMNR

 GHRH-B Ori QQGERNQEQGAA.  73
            ||||||||||||
GHRH-B opti QQGERNQEQGAAC
```

Figure 15

```
 +3  A  M  V   L  W  V  F   F  L  V   T  L  T   L  S  S  G   S  H  G   S  L  P   S  Q  P  L   R  I  P   R  Y  A
   1 GCCATGGTGC TGTGGGTGTT CTTCCTGGTG ACCCTGACCC TGAGCAGCGG AAGCCACGGC AGCCTGCCCA GCCAGCCCCT GAGGATCCCT AGGTACGCCG
     CGGTACCACG ACACCCACAA GAAGGACCAC TGGGACTGGG ACTCGTCGCC TTCGGTGCCG TCGGACGGGT CGGTCGGGGA CTCCTAGGGA TCCATGCGGC

 +3 D  A  I  F   T  N  S   Y  R  K   I  L  G  Q   L  S  A   R  K  L   L  Q  D  I   M  N  R   Q  Q  G   E  R  N  Q
 101 ACGCCATCTT CACCAACAGC TACAGGAAGA TCCTGGGCCA GCTGAGCGCT AGGAAGCTCC TGCAGGACAT CATGAACAGG CAGCAGGGCG AGAGGAACCA
     TGCGGTAGAA GTGGTTGTCG ATGTCCTTCT AGGACCCGGT CGACTCGCGA TCCTTCGAGG ACGTCCTGTA GTACTTGTCC GTCGTCCCGC TCTCCTTGGT

 +3   E  Q  G   A  &  #   A  C
 201 GGAGCAGGGC GCCTGATAAG CTTGC
     CCTCGTCCCG CGGACTATTC GAACG
```

Figure 17

```
GHRH-O Ori  .CCATGGTGCTCTGGGTGTTCTTCCTCGTGACCCTCACCCTCAGCAGCGGCTCCCACGGT  60
             |||||||||| |||||||||||||| |||||||| ||||| ||||||||   |||||| 
GHRH-O opti GCCATGGTGCT**G**TGGGTGTTCTTCCT**G**GTGACCCT**G**ACCCT**G**AGCAGCGG**AAG**CCACGG**C**

GHRH-O Ori  TCCCTGCCTTCCCAGCCTCTCAGGATTCCACGGTACGCCGACGCCATCTTCACCAACAGC  120
              ||||||   |||||| || ||||| ||  |||||||||||||||||||||||||||||
GHRH-O opti **AG**CCTGCC**CAG**CCAGCC**C**CT**G**AGGAT**C**CC**TA**GGTACGCCGACGCCATCTTCACCAACAGC

GHRH-O Ori  TACCGGAAGATCCTGGGCCAGCTGTCCGCCCGGAAGCTGCTGCAGGACATCATGAACAGG  180
            ||| ||||||||||||||||||||  |||  ||||||| |||||||||||||||||||||
GHRH-O opti TAC**A**GGAAGATCCTGGGCCAGCTG**AG**CGC**TA**GGAAGCT**C**CTGCAGGACATCATGAACAGG

GHRH-O Ori  CAGCAGGGCGAGAGAAACCAGGAGCAGGGCGCCTGATAAGCTT..  225
            |||||||||||||| ||||||||||||||||||||||||||||
GHRH-O opti CAGCAGGGCGAGAG**G**AACCAGGAGCAGGGCGCCTGATAAGCTTGC
```

Figure 18

```
GHRH-O Ori  .MVLWVFFLVTLTLSSGSHGSLPSQPLRIPRYADAIFTNSYRKILGQLSARKLLQDIMNR   60
              |||||||||||||||||||||||||||||||||||||||||||||||||||||||||||
GHRH-O opti AMVLWVFFLVTLTLSSGSHGSLPSQPLRIPRYADAIFTNSYRKILGQLSARKLLQDIMNR

GHRH-O Ori  QQGERNQEQGAA.   73
            ||||||||||||
GHRH-O opti QQGERNQEQGAAC
```

Figure 19

```
 +3 A  M  A   L  W  V  F   F  V  L   L  T  L   T  S  G  S   H  C  S   L  P  P   S  P  P  F   R  V  R   R  H  A
  1 GCCATGGCCC TGTGGGTGTT CTTTGTGCTG CTGACCCTGA CCTCCGGAAG CCACTGCAGC CTGCCACCCA GCCCACCCTT CCGCGTCAGG CGCCACGCCG
    CGGTACCGGG ACACCCACAA GAAACACGAC GACTGGGACT GGAGGCCTTC GGTGACGTCG GACGGTGGGT CGGGTGGGAA GGCGCAGTCC GCGGTGCGGC

 +3 D  G  I  F   S  K  A   Y  R  K   L  L  G  Q   L  S  A   R  N  Y   L  H  S  L   M  A  K   R  V  G   S  G  L  G
101 ACGGCATCTT CAGCAAGGCC TACCGCAAGC TCCTGGGCCA GCTGAGCGCA CGCAACTACC TGCACAGCCT GATGGCCAAG CGCGTGGGCA GCGGACTGGG
    TGCCGTAGAA GTCGTTCCGG ATGGCGTTCG AGGACCCGGT CGACTCGCGT GCGTTGATGG ACGTGTCGGA CTACCGGTTC GCGCACCCGT CGCCTGACCC

 +3  D  E  A   E  P  L   S  &  #  A   C
201 AGACGAGGCC GAGCCCCTGA GCTGATAAGC TTGC
    TCTGCTCCGG CTCGGGGACT CGACTATTCG AACG
```

Figure 21

```
GHRH /ori     .CCATGGCACTCTGGGTGTTCTTTGTGCTCCTCACCCTCACCAGTGGCTCCCACTGCTCA   60
              o|||||||o||o||||||||||||||||||o||o|||||o||ooo||ooo|||||||ooo
GHRH/opt-Chi  GCCATGGCCCTGTGGGTGTTCTTTGTGCTGCTGACCCTGACCTCCGGAAGCCACTGCAGC

GHRH /ori     CTGCCCCCCTCACCTCCCTTCAGGGTGCGGCGGCACGCCGATGGGATCTTCAGCAAAGCC  120
              |||||o|||ooo||o||||||o|o||oo||||o||||||||o||o||||||||||||o|||
GHRH/opt-Chi  CTGCCACCCAGCCCACCCTTCCGCGTCAGGCGCCACGCCGACGGCATCTTCAGCAAGGCC

GHRH /ori     TACAGGAAACTCCTGGCCAGCTGTCCGCAAGAAATTACCTGCACTCCCTGATGGCCAAG  180
              |||o|o||o||||||||||||||oo||||o|o||o||||||||||oo|||||||||||||
GHRH/opt-Chi  TACCGCAAGCTCCTGGCCAGCTGAGCGCACGCAACTACCTGCACAGCCTGATGGCCAAG

GHRH /ori     CGGGTCGGCAGCGGCCTGGGGGACGAGGCGGAACCGCTCAGCTGATAAGCTT..  234
              ||o||o||||||||o|||||o||||||||o||o||o||o||||||||||||||oo
GHRH/opt-Chi  CGCGTGGGCAGCGGACTGGGAGACGAGGCCGAGCCCCTGAGCTGATAAGCTTGC
```

Figure 22

```
   GHRH /ori  .MALWVFFVLLTLTSGSHCSLPPSPPFRVRRHADGIFSKAYRKLLGQLSARNYLHSLMAK   60
              o|||||||||||||||||||||||||||||||||||||||||||||||||||||||||||
GHRH/opt-Chi  AMALWVFFVLLTLTSGSHCSLPPSPPFRVRRHADGIFSKAYRKLLGQLSARNYLHSLMAK

   GHRH /ori  RVGSGLGDEAEPLSA.   76
              |||||||||||||||o
GHRH/opt-Chi  RVGSGLGDEAEPLSAC
```

Figure 23

CODON OPTIMIZED SYNTHETIC PLASMIDS

RELATED APPLICATIONS

This application claims priority to U.S. Provisional Patent Application Ser. No. 60/396,247, entitled "Codon Optimized Synthetic Plasmids," filed on Jul. 16, 2002, the entire content of which is hereby incorporated by reference.

BACKGROUND

One aspect of the current invention is an optimized nucleic acid delivery vehicle, or synthetic expression plasmid. The synthetic expression plasmid of this invention has reduced components, and has been optimized to increase efficacy, and reduce adverse reactions in vivo. In addition to a mammalian gene of interest, a typical nucleic acid delivery vehicle or synthetic expression plasmid contains many structural elements necessary for the in vitro amplification of the plasmid in a bacterial host. Consequently, some of the inherent bacterial nucleic acid sequences can cause adverse effects when the amplified plasmid is introduced into a mammalian host. For example, the presence of CpG sequences are known to cause both gene silencing and initiate an immune response in mammals. By utilizing codon optimization, essential bacterial structural elements (e.g. bacterial antibiotic resistant genes) are synthetically constructed and used to replace codons that contained detrimental sequences, but do not effect the final gene product. The current invention involves a "synthetic plasmid backbone" (pAV0201) that provides a clean lineage, which is useful for plasmid supplementation therapy in mammals.

A plasmid based mammalian expression system is minimally composed of a plasmid backbone, a synthetic delivery promoter in addition to the nucleic acid encoding a therapeutic expression product. A plasmid backbone typically contains a bacterial origin of replication, and a bacterial antibiotic selection gene, which are necessary for the specific growth of only the bacteria that are transformed with the proper plasmid. However, there are plasmids, called mini-circles, that lack both the antibiotic resistance gene and the origin of replication (Darquet et al., 1997; Darquet et al., 1999; Soubrier et al., 1999). The use of in vitro amplified expression plasmid DNA (i.e. non-viral expression systems) avoids the risks associated with viral vectors. The non-viral expression systems products generally have low toxicity due to the use of "species-specific" components for gene delivery, which minimizes the risks of immunogenicity generally associated with viral vectors. One aspect of the current invention is a new, versatile, and codon optimized plasmid based mammalian expression system that will reduce the adverse effects associated with prokaryotic nucleic acid sequences in mammalian hosts. In addition, this new plasmid will constitute the base of a species-specific library of plasmids for expression of hormones or other proteins for agricultural and companion animal applications.

Codon optimization: Expression of eukaryotic gene products in prokaryotes is sometimes limited by the presence of codons that are infrequently used in *E. coli*. Expression of such genes can be enhanced by systematic substitution of the endogenous codons with codons over represented in highly expressed prokaryotic genes. Although not wanting to be bound by theory, it is commonly thought that rare codons cause pausing of the ribosome. Pausing of the ribosome can lead to a failure to complete the nascent polypeptide chain and a uncoupling of transcription and translation. Additionally, pausing of the ribosome is thought to expose the 3' end of the mRNA to cellular ribonucleases. An invention thought to circumvented such problems for prokaryotic expression of eukaryotic genes was discussed in U.S. Pat. No. 6,114,148 issued on Sep. 5, 2000 and titled "High level expression of proteins" with Seed, et al., listed as inventors ("the Seed '148 patent"). The Seed '148 patent features a synthetic gene that encodes a protein normally expressed in a mammalian cell wherein a non-preferred codon in the natural gene encoding the protein has been replaced by a preferred codon encoding the same amino acid. In contrast, the use of prokaryotic codons in mammalian systems can lead to detrimental effects (e.g. increased immune response). Furthermore, there are species specific differences with codons that are preferred, or less-preferred among species of a genus (Narum et al., 2001). One aspect of the current invention is the codon optimization of modified mammalian gene sequences. Publicly available databases for optimized codons have been referenced in the following articles: Nagata T, Uchijima M, Yoshida A, Kawashima M, Koide Y. Biochem Biophys Res Commun 261:445-51 (1999). Codon optimization effect on translational efficiency of DNA vaccine in mammalian cells: analysis of plasmid DNA encoding a CTL epitope derived from microorganisms; Uchijima, M, Yoshida, A, Nagata, T, Koide, Y. J Immunol 161:5594-9 (1998). Optimization of codon usage of plasmid DNA vaccine is required for the effective MHC class I-restricted T cell responses against an intracellular bacterium; Meetei, AR and Rao, MR. Protein Expr Purif 13:184-90 (1998). Hyperexpression of rat spermatidal protein TP2 in *Escherichia coli* by codon optimization and engineering the vector-encoded 5' UTR; Andre, S, Seed, B, Eberle, J, Schraut, W, Bultmann, A, Haas, J. J Virol 72:1497-503 (1998). Increased immune response elicited by DNA vaccination with a synthetic gp120 sequence with optimized codon usage; Hale, R S and Thompson, G. Protein Expr Purif 12:185-8 (1998). Codon optimization of the gene encoding a domain from human type 1 neurofibromin protein results in a threefold improvement in expression level in *Escherichia coli*; Hubatsch, I, Ridderstrom, M, Mannervik, B. Biochem J 330:175-9 (1998). Human glutathione transferase A4-4: an alpha class enzyme with high catalytic efficiency in the conjugation of 4-hydroxynonenal and other genotoxic products of lipid peroxidation; Kim, C H, Oh, Y, Lee, T H. Gene 199:293-301 (1997). Codon optimization for high-level expression of human erythropoietin (EPO) in mammalian cells; Deng, T. FEBS Lett 409(2):269-72 (1997). Bacterial expression and purification of biologically active mouse c-Fos proteins by selective codon optimization; Cormack, B P, Bertram, G, Egerton, M, Gow, N A, Falkow, S, Brown, A J. Microbiology 143:303-11 (1997). Yeast-enhanced green fluorescent protein, a reporter of gene expression in *Candida albicans*; Prapunwattana, P, Sirawarapom, W, Yuthavong, Y, Santi, D V. Mol Biochem Parasitol 83:93-106 (1996) Chemical synthesis of the Plasmodium falciparum dihydrofolate reductase-thymidylate synthase gene; Pikaart, M J and Felsenfeld, G. Protein Expr Purif 8:469-75 (1996). Expression and codon usage optimization of the erythroid-specific transcription factor cGATA-1 in baculoviral and bacterial systems; Yang, T T, Cheng, L, Kain, S R. Nucleic Acids Res 24:4592-3 (1996). Optimized codon usage and chromophore mutations provide enhanced sensitivity with the green fluorescent protein; Gouka, R J, Punt, P J, Hessing, J G, van den Hondel, C A. Appl Environ Microbiol 62:1951-7 (1996). Analysis of heterologous protein production in defined recombinant *Aspergillus awamori* strains; Altmann, S W, Timans, J C, Rock, F L, Bazan, J F, Kastelein, R A. Protein Expr Purif 6:722-6 (1995). Expression and purification of a synthetic human obese gene product; Kane, J., Current Opinion in Biotechnology 6:494-500 (1995). Effects of rare codon clusters on gene expression in *Escherichia coli*; Airenne, K J, Sarkkinen, P, Punnonen, E L, Kulomaa, M S. Gene, 144:75-80 (1994). Production of recombinant avidin in *Escherichia coli*; Wang, B Q, Lei, L, Burton, Z F. Protein Expr Purif 5:476-485 (1994). Importance of codon preference for production of human RAP74 and reconstitution of the RAP30/74 complex; Gerchman, S E, Graziano, V, Ramakrishnan, V. Protein Expr Purif 5:242-51 (1994). Expression of chicken linker histones in *E. coli*: sources of problems and methods for overcoming some of the difficulties; Dittrich, W, Williams, K L, Slade, M B. Bio/Technology 12:614-8 (1994). Production and Secretion of Recombinant Proteins in *Dictyostelium discoideum*; Holler, T P, Foltin, S K, Ye, Q Z, Hupe, D J. Gene 136:323-8 (1993). HIV1 integrase expressed in *Escherichia coli* from a synthetic gene; Kane, J F, Violand, B N, Curran, D F, Staten, N R, Duffin, K L, Bogosian, G. Nucleic Acids Res 20:6707-12 (1992). Novel in-frame two codon translational hop during synthesis of bovine placental lactogen in a recombinant strain of *Escherichia coli*; Kotula, Land Curtis, P J. Biotechnology (NY) 9:1386-9(1991). Evaluation of foreign gene codon optimization in yeast: expression of a mouse IG kappa chain; Makoff, A J, Oxer, M D, Romanos, M A, Fairweather, N F, Ballantine, S. Nucleic Acids Res. 17:10191-10202 (1989). Expression of tetanus toxin fragment C in *E. coli*: high level expression by removing rare codons; Misra, R and Reeves, P. Eur J Biochem 152:151-5 (1985). Intermediates in the synthesis of TolC protein include an incomplete peptide stalled at a rare Arg codon; Robinson, M, Lilley, R, Little, S, Emtage, J S, Yarranton, G, Stephens, P, Millican, A, Eaton, M, Humphreys, G. Nucleic Acids Res 12:6663-71 (1984). Codon usage can affect efficiency of translation of genes in *Escherichia coli*; Pedersen, S. EMBO J 3:2895-8 (1984). *Escherichia coli* ribosomes translate in vivo with variable rate.

As mentioned above, a plasmid backbone typically contains a bacterial origin of replication, and a bacterial antibiotic selection gene, which are necessary for the specific growth of only the bacteria that are transformed with the proper plasmid. However, the nucleotide sequence of the bacterial gene products can adversely affect a mammalian host receiving plasmid DNA. For example, it was desirable to avoid CpG sequences, as these sequences have been shown to cause a recipient host to have an immune response (Manders and Thomas, 2000; Scheule, 2000) to plasmids as well as possible gene silencing (Shi et al., 2002; Shiraishi et al., 2002). Thus, the DNA coding regions of any expressed genes avoid the “cg” sequence, without changing the amino acid sequence. Another aspect of the current invention involves the removal of unnecessary DNA sequences that were left over from prior cloning procedures. As a result of codon optimization, and removal of unnecessary DNA sequences, a synthetically generated plasmid backbone (“pAV0201”) with a unique cloning site that was constructed to generate a clean lineage of plasmid, which will be useful for plasmid mediated gene supplementation.

Growth Hormone (“GH”) and Immune Function: Another aspect of the current invention is utilizing the synthetically generated plasmid backbone pAV0201 for plasmid mediated gene supplementation. The central role of growth hormone (“GH”) is controlling somatic growth in humans and other vertebrates, and the physiologically relevant pathways regulating GH secretion from the pituitary is well known (Berneis and Keller, 1996). The GH production pathway is composed of a series of interdependent genes whose products are required for normal growth (Cuttler, 1996). The GH pathway genes include: (1) ligands, such as GH and insulin-like growth factor-I (“IGF-I”); (2) transcription factors such as prophet of pit 1, or prop 1, and pit 1: (3) agonists and antagonists, such as growth hormone releasing hormone (“GHRH”) and somatostatin (“SS”), respectively; and (4) receptors, such as GHRH receptor (“GHRH-R”) and the GH receptor (“GH-R”). These genes are expressed in different organs and tissues, including the hypothalamus, pituitary, liver, and bone. Effective and regulated expression of the GH pathway is essential for optimal linear growth, as well as homeostasis of carbohydrate, protein, and fat metabolism GH synthesis and secretion from the anterior pituitary is stimulated by GHRH and inhibited by somatostatin, both hypothalamic hormones (Frohman et al., 1992). GH increases production of IGF-I, primarily in the liver, and other target organs. IGF-I and GH, in turn, feedback on the hypothalamus and pituitary to inhibit GHRH and GH release. GH elicits both direct and indirect actions on peripheral tissues, the indirect effects being mediated mainly by IGF-I.

The immune function is modulated by IGF-I (Geffner, 1997; LeRoith et al., 1996), which has two major effects on B cell development: potentiation and maturation, and as a B-cell proliferation cofactor that works together with interlukin-7 (“IL-7”). These activities were identified through the use of anti-IGF-I antibodies, antisense sequences to IGF-I, and the use of recombinant IGF-I to substitute for the activity. There is evidence that macrophages are a rich source of IGF-I. The treatment of mice with recombinant IGF-I confirmed these observations as it increased the number of pre-B and mature B cells in bone marrow. The mature B cell remained sensitive to IGF-I as immunoglobulin production was also stimulated by IGF-I in vitro and in vivo.

The production of recombinant proteins in the last 2 decades provided a useful tool for the treatment of many diverse conditions. For example, GH-deficiencies in short stature children, anabolic agent in burn, sepsis, and AIDS patients (Carrel and Allen, 2000; Hart et al., 2001; Lal et al., 2000; Mulligan et al., 1999). However, resistance to GH action has been reported in malnutrition and infection (Kotzmann et al., 2001). Long-term studies on transgenic animals and in patients undergoing GH therapies have shown no correlation in between GH or IGF-I therapy and cancer development. GH replacement therapy is widely used clinically, with beneficial effects, but therapy is associated with several disadvantages (Blethen, 1995): GH must be administered subcutaneously or intramuscularly once a day to three times a week for months, or usually years; insulin resistance and impaired glucose tolerance (Burgert et al., 2002); accelerated bone epiphysis growth and closure in pediatric patients (Blethen and Rundle, 1996).

In contrast, essentially no side effects have been reported for recombinant GHRH therapies. Extracranially secreted GHRH, as mature peptide or truncated molecules (as seen with pancreatic islet cell tumors and variously located carcinoids) are often biologically active and can even produce acromegaly (Faglia et al., 1992; Melmed, 1991). Administration of recombinant GHRH to GH-deficient children or adult humans augments IGF-I levels, increases GH secretion proportionally to the GHRH dose, yet still invokes a response to bolus doses of recombinant GHRH (Bercu et al., 1997). Thus, GHRH administration represents a more physiological alternative of increasing subnormal GH and IGF-I levels (Corpas et al., 1993b).

GH is released in a distinctive pulsatile pattern that has profound importance for its biological activity. Secretion of GH is stimulated by the GHRH, and inhibited by somatostatin, and both hypothalamic hormones. GH pulses are a result of GHRH secretion that is associated with a diminution or withdrawal of somatostatin secretion. In addition, the pulse generator mechanism is timed by GH-negative feedback. The endogenous rhythm of GH secretion becomes entrained to the imposed rhythm of exogenous GH administration. Effective and regulated expression of the GH and insulin-like growth factor-I ("IGF-I") pathway is essential for optimal linear growth, homeostasis of carbohydrate, protein, and fat metabolism, and for providing a positive nitrogen balance. Numerous studies in humans, sheep or pigs showed that continuous infusion with recombinant GHRH protein restores the normal GH pattern without desensitizing GHRH receptors or depleting GH supplies as this system is capable of feed-back regulation, which is abolished in the GH therapies. Although recombinant GHRH protein therapy entrains and stimulates normal cyclical GH secretion with virtually no side effects (Duck et al., 1992), the short half-life of GHRH in vivo requires frequent (one to three times a day) intravenous, subcutaneous or intranasal (requiring 300-fold higher dose) administration (Evans et al., 1985). Thus, as a chronic treatment, GHRH administration is not practical.

Wild type GHRH has a relatively short half-life in the circulatory system, both in humans and in farm animals (Frohman et al., 1986). After 60 minutes of incubation in plasma 95% of the GHRH(1-44)$NH_2$ is degraded, while incubation of the shorter (1-40)OH form of the hormone, under similar conditions, shows only a 77% degradation of the peptide after 60 minutes of incubation (Frohman et al., 1989a). Incorporation of cDNA coding for a particular protease-resistant GHRH analog in a gene therapy vector results in a molecule with a longer half-life in serum (Draghia-Akli et al., 1999), increased potency, and provides greater GH release in plasmid-injected animals as described in in U.S. Pat. No. 6,551,996 that was issued on Apr. 23, 2003 titled "Super Active Porcine Growth Hormone Releasing Hormone Analog" with Schwartz, et al., listed as inventors, ("the Schwartz '996 patent"), the entire content is herein incorporated by reference. The Schwartz '996 patent teaches that an application of a GHRH analog containing mutations that improve the ability to elicit the release of growth hormone. In addition, the Schwartz '996 patent relates to the treatment of growth deficiencies; the improvement of growth performance; the stimulation of production of growth hormone in an animal at a greater level than that associated with normal growth; and the enhancement of growth utilizing the administration of growth hormone releasing hormone analog and is herein incorporated by reference. Mutagenesis via amino acid replacement of protease sensitive amino acids prolongs the serum half-life of the GHRH molecule. Furthermore, the enhancement of biological activity of GHRH is achieved by using super-active analogs that may increase its binding affinity to specific receptors as described in the Schwartz '996 patent.

Extracranially secreted GHRH, as processed protein species GHRH(1-40) hydroxy or GHRH(1-44) amide or even as shorter truncated molecules, are biological active. It has been reported that a low level of GHRH (100 pg/ml) in the blood supply stimulates GH secretion (Corpas et al., 1993a). Direct plasmid DNA gene transfer is currently the basis of many emerging therapeutic strategies and thus does not require viral genes or lipid particles (Aihara and Miyazaki, 1998; Lesbordes et al., 2002). Skeletal muscle is a target tissue because muscle fiber has a long life span and can be transduced by circular DNA plasmids that express over months or years in an immunocompetent host (Danko and Wolff, 1994; Wolff et al., 1992). Previous reports demonstrated that human GHRH cDNA could be delivered to muscle by an injectable myogenic expression vector in mice where it transiently stimulated GH secretion over a period of two weeks in immunocompetent mice (Draghia-Akli et al., 1997), and for 5 month in immunodeficient mice (Draghia-Akli et al., 2002)(human hormones are immunogenic in normal immunocompetent rodents, and transgene expression is transitory in these cases).

U.S. Pat. No. 5,061,690 issued on Oct. 29, 1991 and titled "Method for increasing milk production in mammals and/or increasing the birth weight of their newborn and improving postnatal growth "with Kann, et al., listed as inventors, ("the Kann '690 patent"). The Kann '690 patent is directed toward increasing both birth weight and milk production by supplying to pregnant female mammals an effective amount of human GHRH or one of it analogs for 10-20 days. Application of the analogs lasts only throughout the lactation period. However, multiple administrations are presented, and there is no teachings regarding administration of the growth hormone releasing hormone a nucleic acid delivery vehicle or a codon optimized synthetic mammalian expression plasmid.

U.S. Pat. No. 5,134,120 issued on Jul. 28, 1992 and titled "Use of growth hormone to enhance porcine weight gain" with Boyd, et al., listed as inventors, ("the Boyd '120 patent"); and U.S. Pat. No. 5,292,721 issued on Mar. 8, 1994 and titled "Use of growth hormone to enhance porcine fetal energy and sow lactation performance" with Boyd, et al., listed as inventors, ("the Boyd '721 patent"). Both the Boyd '120, and Boyd 721 patent teach that by deliberately increasing growth hormone in swine during the last 2 weeks of pregnancy through a 3 week lactation resulted in the newborn piglets having marked enhancement of the ability to maintain plasma concentrations of glucose and free fatty acids when fasted after birth. In addition, the Boyd '120 and Boyd '721 patents teach that treatment of the sow during lactation results in increased milk fat in the colostrum and an increased milk yield. These effects are important in enhancing survivability of newborn pigs and weight gain prior to weaning. However Boyd '120 and Boyd '721 patents provide no teachings regarding administration of the growth hormone releasing hormone a nucleic acid delivery vehicle or a codon optimized synthetic mammalian expression plasmid.

In summary, previous studies have shown that it is possible to treat various disease conditions in a limited capacity utilizing recombinant protein technology, but these treatments have some significant drawbacks. It has also been taught that nucleic acid expression plasmids that encode recombinant proteins are viable solutions to the problems of frequent injections and high cost of traditional recombinant therapy. However, the nucleic acid expression plasmids also have some drawbacks when injected into a mammalian host. The synthetic plasmids of this invention have reduced components, and have been codon optimized to increase efficacy, and reduce adverse reactions in vivo. The introduction of point mutations in to the encoded recombinant proteins was a significant step forward in producing proteins that are more stable in vivo than the wild type counterparts. Since there is a need in the art to expanded treatments for subjects with a disease by utilizing nucleic acid expression constructs that are delivered into a subject and express stable therapeutic proteins in vivo, the combination of codon optimization of an encoded therapeutic mammalian gene in an optimized plasmid backbone will further enhance the art of plasmid mediated gene supplementation.

SUMMARY

One aspect of the current invention is an optimized synthetic mammalian expression plasmid (e.g. pAV0201). This new plasmid comprises a therapeutic element, and a replication element. The therapeutic element of the new plasmid comprises a eukaryotic promoter; a 5' untranslated region ("UTR"); a codon-optimized-eukaryotic therapeutic gene sequence; and a polyadenylation signal. The therapeutic elements of this plasmid are operatively linked and located in a first operatively-linked arrangement. Additionally, the optimized synthetic mammalian expression plasmid comprises replication elements, wherein the replication elements are operatively linked and located in a second operatively-linked arrangement. The replication elements comprise a selectable marker gene promoter, a ribosomal binding site, a optimized selectable marker gene sequence, and an origin of replication. The first-operatively-linked arrangement and the second-operatively-linked arrangement comprise a circular structure of the codon optimized synthetic mammalian expression plasmid.

In preferred embodiments, the synthetic mammalian expression plasmid comprises a pUC-18 prokaryotic origin of replication sequence. However, the origin of replication may also comprise an autonomously replication sequence ("ARS"). In a preferred embodiment, the optimized prokaryotic antibiotic resistant gene comprises kanamycin. In another preferred embodiment, the poly adenylation signal ("PolyA") comprises a human growth hormone ("hGH") poly A signal, and a hGH 5' untranslated region ("5'UTR"). The codon optimized mammalian therapeutic gene sequence comprises a sequence that encodes a modified species specific growth hormone releasing hormone ("GHRH"). In preferred embodiments, the codon optimized sequence comprises porcine, mouse, rat, bovine, ovine, and chicken GHRH (e.g. SEQ ID NO: 4, SEQ ID NO: 5; SEQ ID NO: 6; SEQ ID NO: 7; SEQ ID NO: 8; and SEQ ID NO: 9). Similarly, species specific, and codon optimized plasmids are disclosed (e.g. SEQ ID NO: 17; SEQ ID NO: 18; SEQ ID NO: 19; SEQ ID NO: 20; and SEQ ID NO: 21).

Another aspect of the current invention is a method for plasmid mediated gene supplementation that comprises delivering a codon optimized synthetic mammalian expression plasmid into a subject. The codon optimized synthetic mammalian expression plasmid encodes a growth hormone releasing hormone ("GHRH") or functional biological equivalent in the subject. The method of delivering the codon optimized synthetic mammalian expression plasmid into the cells of the subject is via electroporation. In a preferred embodiment, the cells of the subject can be somatic cells, stem cells, or germ cells. The codon optimized synthetic mammalian expression plasmids consisting of SEQ ID NO: 17, SEQ ID NO: 18, SEQ ID NO: 19, SEQ ID NO: 20, and SEQ ID NO: 21 have been contemplated by the inventors. The encoded GHRH is a biologically active polypeptide; and the encoded functional biological equivalent of GHRH is a polypeptide that has been engineered to contain a distinct amino acid sequence while simultaneously having similar or improved biologically activity when compared to the GHRH polypeptide. One result of expressing the encoded GHRH or functional biological equivalent thereof in a subject is the facilitation of growth hormone ("GH") secretion in the subject.

BRIEF DESCRIPTION OF FIGURES

FIG. 3 shows the optimized nucleic acid sequence for the kanamycin gene (SEQ ID NO: 3) and the corresponding translated amino acid sequence (SEQ ID NO: 22);

FIG. 5 shows the optimized nucleic acid sequence for the mGHRH gene (SEQ ID NO: 5) and the corresponding translated amino acid sequence (SEQ ID NO: 23);

FIG. 6 shows the optimized nucleic acid sequence for the original mGHRH gene ("GHRH-m-ori") (SEQ ID NO: 24), and the optimized mGHRH gene ("GHRH-m-opt") (SEQ ID NO: 5) after removing some CpG islands and other motifs that can decrease protein expression, the changes did not effect the amino acid sequence;

FIG. 7 shows a comparison of the translated amino acid sequence from the original ("GHRH-m-Ori") (SEQ ID NO: 25) and optimized nucleic acid sequence for the mouse GHRH gene ("GHRH-m-Opti") (SEQ ID NO: 23);

FIG. 9 shows the optimized nucleic acid sequence for the rGHRH gene (SEQ ID NO: 6) and the corresponding translated amino acid sequence (SEQ ID NO: 26);

FIG. 10 shows the optimized nucleic acid sequence for the original rGHRH gene ("GHRH-R-ori") (SEQ ID NO: 27), and the optimized rGHRH gene ("GHRH-R-opt") (SEQ ID NO: 6) after removing some CpG islands and other motifs that can decrease protein expression, the changes did not effect the amino acid sequence;

FIG. 11 shows a comparison of the translated amino acid sequence from the original ("GHRH-R-Ori") (SEQ ID NO: 28) and optimized nucleic acid sequence for the rat GHRH gene ("GHRH-R-Opti") (SEQ ID NO: 26);

FIG. 13 shows the optimized nucleic acid sequence for the bGHRH gene (SEQ ID NO: 7) and the corresponding translated amino acid sequence (SEQ ID NO: 29);

FIG. 14 shows the optimized nucleic acid sequence for the original bGHRH gene ("GHRH-B-ori") (SEQ ID NO: 30), and the optimized bGHRH gene ("GHRH-B-opt") (SEQ ID NO: 7) after removing some CpG islands and other motifs that can decrease protein expression, the changes did not effect the amino acid sequence;

FIG. 15 shows a comparison of the translated amino acid sequence from the original ("GHRH-B-Ori") (SEQ ID NO: 31) and optimized nucleic acid sequence for the bovine GHRH gene ("GHRH-B-Opti") (SEQ ID NO: 29);

FIG. 17 shows the optimized nucleic acid sequence for the oGHRH gene (SEQ ID NO: 8) and the corresponding translated amino acid sequence (SEQ ID NO: 32);

FIG. 18 shows the optimized nucleic acid sequence for the original oGHRH gene ("GHRH-O-ori") (SEQ ID NO: 33), and the optimized oGHRH gene ("GHRH-O-opt") (SEQ ID NO: 8) after removing some CpG islands and other motifs that can decrease protein expression, the changes did not effect the amino acid sequence;

FIG. 19 shows a comparison of the translated amino acid sequence from the original ("GHRH-O-Ori") (SEQ ID NO: 34) and optimized nucleic acid sequence for the ovine GHRH gene ("GHRH-O-Opti") (SEQ ID NO: 32);

FIG. 21 shows the optimized nucleic acid sequence for the cGHRH gene (SEQ ID NO: 35) and the corresponding translated amino acid sequence (SEQ ID NO: 36);

FIG. 22 shows the optimized nucleic acid sequence for the original cGHRH gene ("GHRH-Chi-ori") (SEQ ID NO: 37), and the optimized cGHRH gene ("GHRH-Chi-opt") (SEQ ID NO: 35) after removing some CpG islands and other motifs that can decrease protein expression, the changes did not effect the amino acid sequence;

FIG. 23 shows a comparison of the translated amino acid sequence from the original ("GHRH-Chi-Ori") (SEQ ID NO: 38) and optimized nucleic acid sequence for the chicken GHRH gene ("GHRH-Chi-Opti") (SEQ ID NO: 36).

DETAILED DESCRIPTION OF PREFERRED EMBODIMENTS

Figure 1:
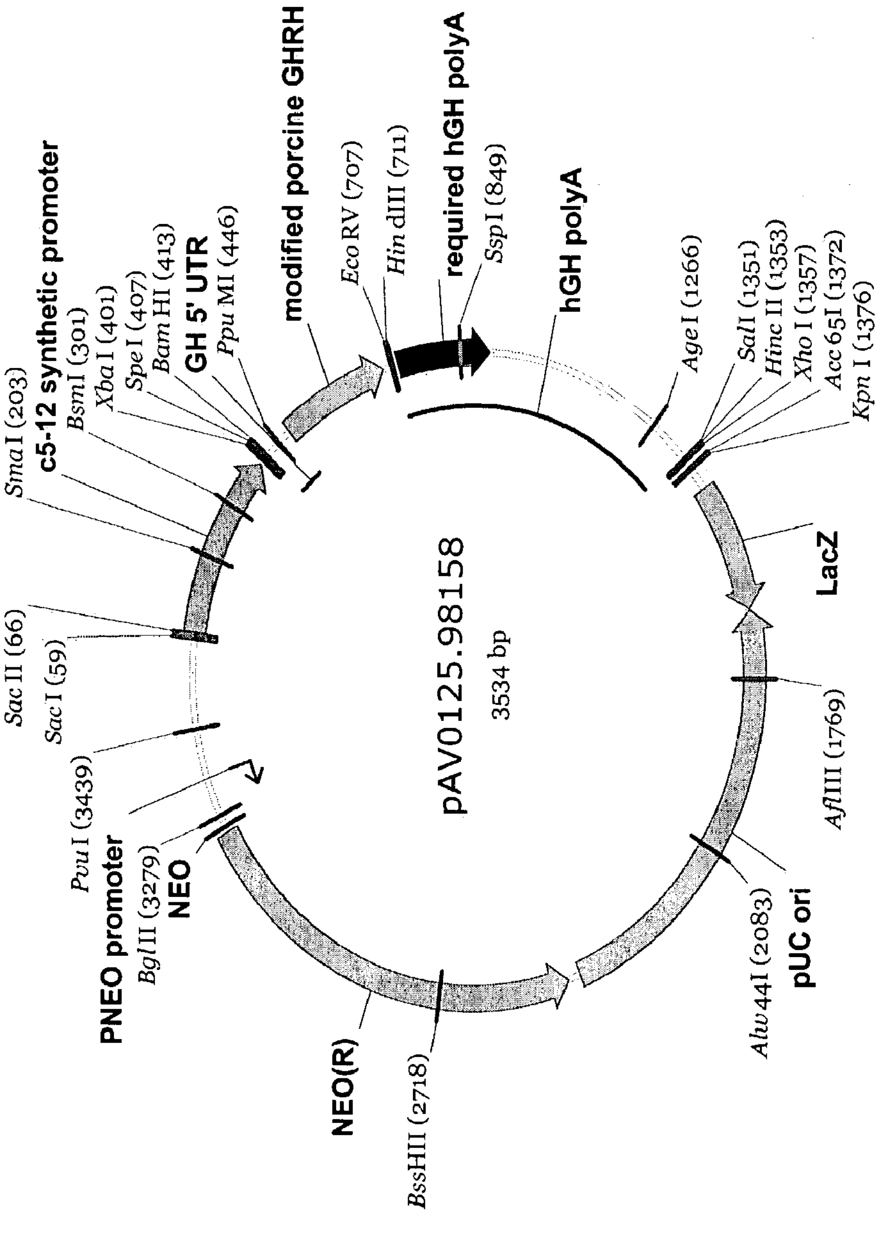
FIG. 1 shows a general map of a plasmid construct (pAV0125, this plasmid contains the porcine modified HV-GHRH sequence) used prior construction of an optimized synthetic plasmid of the current invention.

Terms:

The term "coding region" as used herein refers to any portion of the DNA sequence that is transcribed into messenger RNA (mRNA) and then translated into a sequence of amino acids characteristic of a specific polypeptide.

The term "analog" as used herein includes any mutant of GHRH, or synthetic or naturally occurring peptide fragments of GHRH.

The term "codon" as used herein refers to any group of three consecutive nucleotide bases in a given messenger RNA molecule, or coding strand of DNA that specifies a particular amino-acid, a starting or stopping signal for translation. The term codon also refers to base triplets in a DNA strand.

The term "delivery" as used herein is defined as a means of introducing a material into a subject, a cell or any recipient, by means of chemical or biological process, injection, mixing, electroporation, sonoporation, or combination thereof, either under or without pressure.

The term "encoded GHRH" as used herein is a biologically active polypeptide.

The term "functional biological equivalent" of GHRH as used herein is a polypeptide that has been engineered to contain a distinct amino acid sequence while simultaneously having similar or improved biologically activity when compared to the GHRH polypeptide.

The term "heterologous nucleic acid sequence" as used herein is defined as a DNA sequence consisting of differing regulatory and expression elements.

The term "growth hormone" ("GH") as used herein is defined as a hormone that relates to growth and acts as a chemical messenger to exert its action on a target cell.

The term "growth hormone releasing hormone" ("GHRH") as used herein is defined as a hormone that facilitates or stimulates release of growth hormone, and in a lesser extent other pituitary hormones, as prolactin.

The term "non-optimized codon" as used herein refers to a codon that does not have a match codon frequencies in target and host organisms. The non-optimized codons of this invention were determined using Aptagen's Gene Forge® codon optimization and custom gene synthesis platform (Aptagen, Inc., 2190 Fox Mill Rd. Suite 300, Herndon, Va. 20171). Other publicly available databases for optimized codons are available and will work equally as well.

The term "nucleic acid expression construct" as used herein refers to any type of genetic construct comprising a nucleic acid coding for a RNA capable of being transcribed. The term "expression vector" or "expression plasmid" can also be used interchangeably.

The term "operatively linked" as used herein refers to elements or structures in a nucleic acid sequence that are linked by operative ability and not physical location. The elements or structures are capable of, or characterized by accomplishing a desired operation. It is recognized by one of ordinary skill in the art that it is not necessary for elements or structures in a nucleic acid sequence to be in a tandem or adjacent order to be operatively linked.

The term "optimized codon" as used herein refers to a codon that has a match codon frequencies in target and host organisms, but does not alter the amino acid sequence of the original translated protein. The optimized codons of this invention were determined using Aptagen's Gene Forge® codon optimization and custom gene synthesis platform (Aptagen, Inc., 2190 Fox Mill Rd. Suite 300, Herndon, Va. 20171). Other publicly available databases for optimized codons are available and will work equally as well.

The term "optimized nucleic acid delivery vehicle" as used herein refers to any vector that delivers a nucleic acid into a cell or organism wherein at least one of the codons has been optimized for expression in a host organism. The term "synthetic expression plasmid" can also be used interchangeably with the term optimized nucleic acid delivery vehicle.

The term "promoter" as used herein refers to a sequence of DNA that directs the transcription of a gene. A promoter may direct the transcription of a prokaryotic or eukaryotic gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "replication element" as used herein comprises nucleic acid sequences that will lead to replication of a plasmid in a specified host. One skilled in the art of molecular biology will recognize that the replication element may include, but is not limited to a selectable marker gene promoter, a ribosomal binding site, a selectable marker gene sequence, and a origin of replication.

The term "subject" as used herein refers to any species of the animal kingdom. In preferred embodiments it refers more specifically to humans and animals used for: pets (e.g. cats, dogs, etc.); work (e.g. horses, cows, etc.); food (chicken, fish, lambs, pigs, etc); and all others known in the art.

The term "therapeutic element" as used herein comprises nucleic acid sequences that will lead to an in vivo expression of an encoded gene product. One skilled in the art of molecular biology will recognize that the therapeutic element may include, but is not limited to a promoter sequence, a poly A sequence, or a 3' or 5' UTR.

The term "vector" as used herein refers to any vehicle that delivers a nucleic acid into a cell or organism. Examples include plasmid vectors, viral vectors, liposomes, or cationic lipids.

The new synthetic constructs of the current invention are injected intramuscularly into a correspondent species. For example, the bovine GHRH ("bGHRH") construct is utilized in cows, and ovine GHRH ("oGHRH") construct is utilized in sheep. Although not wanting to be bound by theory, the ovine GHRH will be produced by the sheep muscle fibers, and then delivered into the circulatory system. The circulating hormone will enhance the synthesis and secretion of ovine growth hormone in the anterior pituitary. The new synthetic constructs can promote long-term expression because the new plasmid backbone lacks CpG islands and other bacterial components that alert the immune system of the presence of a foreign antigen. By decreasing the immune response against the plasmid fragment and its products can function in the muscle cells for longer durations of time, which lowers cost of treatment by decreasing the number of treatments. Furthermore, the usage of species-specific transgene will ensure long term expression by the lack of neutralizing antibodies against a foreign GHRH.

Plasmid mediated gene supplementation. The delivery of specific genes to somatic tissue in a manner that can correct inborn or acquired deficiencies and imbalances has been demonstrated in prior art. Plasmid mediated gene supplementation offers a number of advantages over the administration of recombinant proteins. These advantages include the conservation of native protein structure, improved biological activity, avoidance of systemic toxicities, and avoidance of infectious and toxic impurities. In addition, plasmid mediated gene supplementation allows for prolonged exposure to the protein in the therapeutic range, because the newly secreted protein is present continuously in the blood circulation.

Although not wanting to be bound by theory, the primary limitation of using a recombinant protein is the limited availability of protein after each administration. Plasmid mediated gene supplementation using injectable DNA plasmid expression vectors overcomes this drawback, because a single injection into the subject's skeletal muscle permits physiologic expression for extensive periods of time. Injection of the vectors can promote the production of enzymes and hormones in animals in a manner that more closely mimics the natural process. Furthermore, among the non-viral techniques for gene transfer in vivo, the direct injection of plasmid DNA into muscle tissue is simple, inexpensive, and safe.

In a plasmid based expression system, a non-viral gene vector may be composed of a synthetic gene delivery system in addition to the nucleic acid encoding a therapeutic gene product. In this way, the risks associated with the use of most viral vectors can be avoided. Additionally, no integration of plasmid sequences into host chromosomes has been reported in vivo to date, so that this type of gene transfer should neither activate oncogenes nor inactivate tumor suppressor genes. As episomal systems residing outside the chromosomes, plasmids have defined pharmacokinetics and elimination profiles, leading to a finite duration of gene expression in target tissues.

One aspect of the current invention is a new, versatile, and codon optimized plasmid based mammalian expression system that will reduce the adverse effects associated with prokaryotic nucleic acid sequences in mammalian hosts. In addition, this new plasmid will constitute the base of a species-specific library of plasmids for expression of hormones or other proteins for agricultural and companion animal applications. The synthetic expression plasmid of this invention has reduced components, and has been optimized to increase efficacy, and reduce adverse reactions in vivo. In addition to a mammalian gene of interest, a typical nucleic acid delivery vehicle or synthetic expression plasmid contains many structural elements useful for the in vitro amplification of the plasmid in a bacterial host. Consequently, some of the inherent bacterial nucleic acid sequences can cause adverse effects when the amplified plasmid is introduced into a mammalian host. For example, the presence of CpG sequences are known to cause both gene silencing and initiate an immune response in mammals. By utilizing codon optimization, essential bacterial structural elements (e.g. bacterial antibiotic resistant genes) are synthetically constructed and used to replace codons that contained detrimental sequences, but do not effect the final gene product. The current invention involves a "synthetic plasmid backbone" (pAV0201) that provides a clean lineage, which is useful for plasmid supplementation therapy in mammals.

A plasmid based mammalian expression system is minimally composed of a plasmid backbone, a synthetic delivery promoter in addition to the nucleic acid encoding a therapeutic expression product. A plasmid backbone typically contains a bacterial origin of replication, and a bacterial antibiotic selection gene, which are necessary for the specific growth of only the bacteria that are transformed with the proper plasmid. However, there are plasmids that lack both the antibiotic resistance gene and the origin of replication, such plasmids are called mini-circles (Darquet et al., 1997; Darquet et al., 1999; Soubrier et al., 1999). The use of in vitro amplified expression plasmid DNA (i.e. non-viral expression systems) avoids the risks associated with viral vectors. The non-viral expression systems products generally have low toxicity due to the use of "species-specific" components for gene delivery, which minimizes the risks of immunogenicity generally associated with viral vectors. One aspect of the current invention is a new, versatile, and codon optimized plasmid based mammalian expression system, which will constitute the base of a species-specific library of plasmids for expression of hormones or other proteins for agricultural and companion animal applications. For example, optimized synthetic sequences can be produced such that codon frequencies are matched in target and host organisms to ensure proper folding. A bias of GC content can be used to increase mRNA stability or reduce secondary structures. Tandem repeat codons or base runs that may impair the gene can be minimized with codon optimization. Modification of ribosome binding sites and mRNA degradation sites can be utilized. Optimization can also reduce or eliminate problem secondary structures within the transcribed mRNA.

Vectors. One skilled in the art recognizes that expression vectors derived from various bacterial plasmids may be used for delivery of nucleotide sequences to a targeted organ, tissue or cell population. Methods which are well known to those skilled in the art can be used to construct recombinant vectors that will express a gene of interest or a gene encoding a growth hormone releasing hormone analog. Transient expression may last for a month or more with a non-replicating vector and even longer if appropriate replication elements are a part of the vector system, wherein the term "vector" is used to refer to a carrier nucleic acid molecule into which a nucleic acid sequence can be inserted for introduction into a cell where the vector can be replicated and the nucleic acid sequence can be expressed. The term vector can also be referred to as a nucleic acid construct. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, and artificial chromosomes (e.g., YACs). One of skill in the art would be well equipped to construct a vector through standard recombinant techniques, which are described in Maniatis et al., 1988 the entirety is incorporated herein by reference. The selected expressed nucleic acid sequences of a constructed vector could then be codon optimized as described below.

The term "expression vector" refers to a vector or nucleic acid expression construct containing a nucleic acid sequence coding for at least part of a gene product capable of being transcribed. In a specific embodiment the nucleic acid sequence encodes part or all of GHRH. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

In a preferred embodiment, the nucleic acid construction construct or vector of the present invention is a plasmid which comprises a synthetic myogenic (muscle-specific) promoter, a synthetic nucleotide sequence encoding a growth hormone releasing hormone or its analog, and a 3' untranslated region. In other alternative embodiments, optimized porcine growth hormone, optimized human growth hormone, optimized mouse growth hormone, optimized rat growth hormone, optimized bovine growth hormone, optimized ovine growth hormone, optimized chicken growth hormone, or skeletal alpha actin 3' untranslated regions are utilized in the vector.

Promoters and Enhancers. A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one of naturally-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™. Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. In a specific embodiment the promoter is a synthetic myogenic promoter.

The identity of tissue-specific promoters or elements, as well as assays to characterize their activity, is well known to those of skill in the art. Examples of such regions include the human LIMK2 gene, the somatostatin receptor 2 gene, murine epididymal retinoic acid-binding gene, human CD4, mouse alpha2 (XI) collagen, D1A dopamine receptor gene, insulin-like growth factor II, human platelet endothelial cell adhesion molecule-1.

Initiation Signals and Internal Ribosome Binding Sites. A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Multiple Cloning Sites. Vectors can include a multiple cloning site ("MCS"), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing Sites. Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression.

Polyadenylation Signals. In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the bovine or human growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

Origins of Replication. In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Selectable and Screenable Markers. In certain embodiments of the invention, the cells that contain the nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker, such as the antibiotic resistance gene on the plasmid constructs (such as kanamycin, ampicylin, gentamycin, tetracycline, or chloramphenicol).

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

The invention may be better understood with reference to the following examples, which are representative of some of the embodiments of the invention, and are not intended to limit the invention.

EXAMPLE 1

Figure 2:
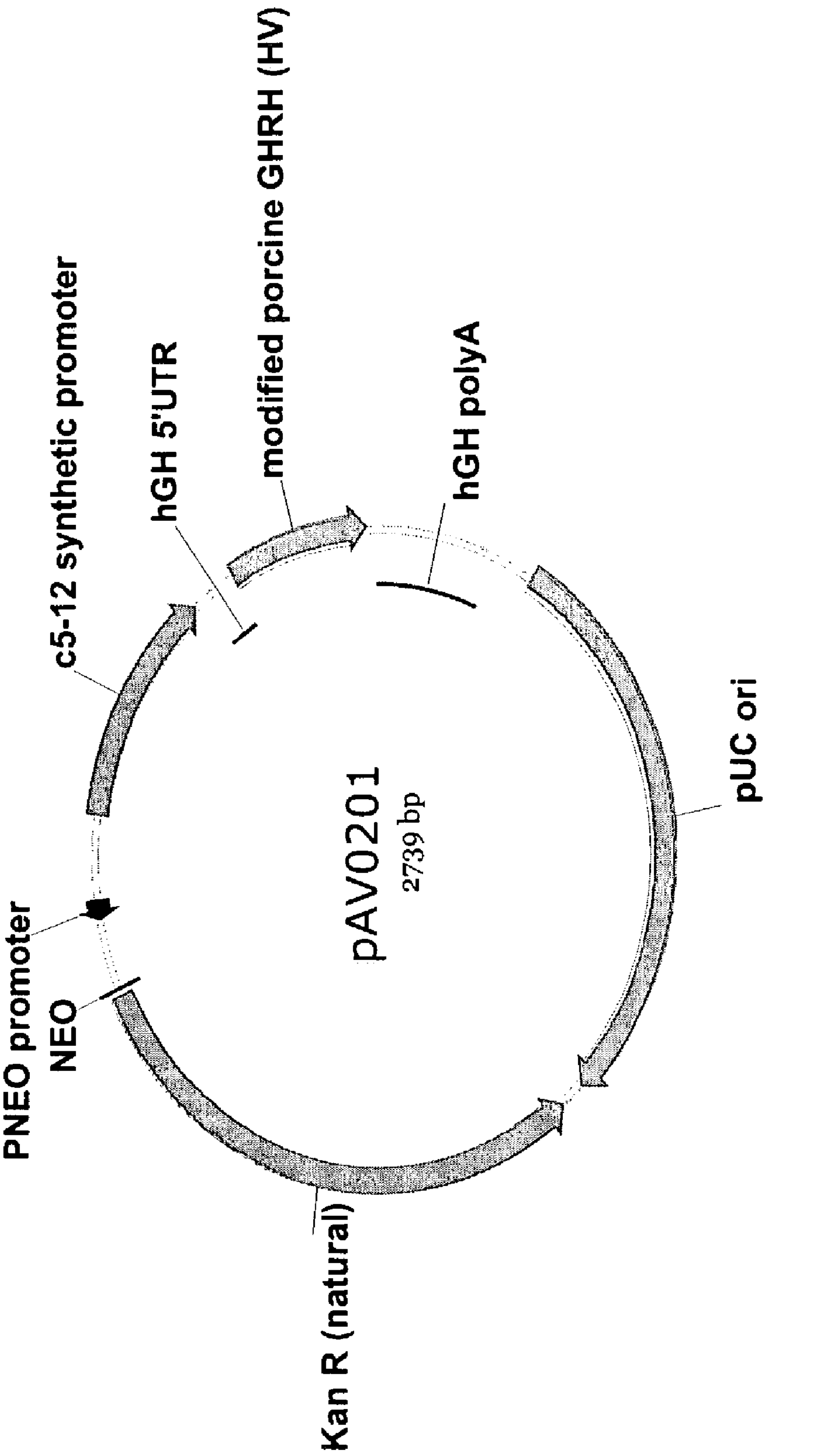
FIG. 2 shows a general map of a synthetic plasmid construct (pAV0201, this construct contains the porcine modified GHRH called HV-GHRH) of the current invention, which contains codon optimization.

Optimized Plasmid Backbone. One aspect of the current invention is the optimized plasmid backbone. The new synthetic plasmids presented below contain eukaryotic sequences that are synthetically optimized for species specific mammalian transcription. An existing pSP-HV-GHRH plasmid ("pAV0125") SEQ ID NO: 1), as shown in FIG. 1 was synthetically optimized to form a new plasmid ("pAV0201") SEQ ID NO: 2). The plasmid pAV0125 was described in U.S. Pat. No. 6,551,996 that was issued on Apr. 23, 2003 titled "Super Active Porcine Growth Hormone Releasing Hormone Analog" with Schwartz, et al., listed as inventors, ("the Schwartz '996 Patent"). This 3,534 bp plasmid pAV0125 SEQ ID NO: 1) contains a plasmid backbone with various component from different commercially available plasmids, for example, a synthetic promoter SPc5-12 SEQ ID NO: 15), a modified porcine GHRH sequence SEQ ID NO: 4), and a 3' end of human growth hormone SEQ ID NO: 10). The new optimized synthetic expression vector SEQ ID NO: 2) contains 2,739 bp and is shown in FIG. 2. The therapeutic encoded gene for the optimized plasmid in FIG. 2 may also include optimized nucleic acid sequences that encode the following modified GHRH molecules.

ENCODED GHRH AMINO ACID SEQUENCE

| | | |
|---|---|---|
| wt-GHRH | **YA**DAIFTNSYRKVL**G**QLSARKLLQDI**MS**RQQGERNQEQGA-OH | (SEQ ID NO:39) |
| HV-GHRH | **HV**DAIFTNSYRKVL**A**QLSARKLLQDI**LN**RQQGERNQEQGA-OH | (SEQ ID NO:40) |
| TI-GHRH | **YI**DAIFTNSYRKVL**A**QLSARKLLQDI**LN**RQQGERNQEQGA-OH | (SEQ ID NO:41) |
| TV-GHRH | **YV**DAIFTNSYRKVL**A**QLSARKLLQDI**LN**RQQGERNQEQGA-OH | (SEQ ID NO:42) |
| 15/27/28-GHRH | **YA**DAIFTNSYRKVL**A**QLSARKLLQDI**LN**RQQGERNQEQGA-OH | (SEQ ID NO:43) |

In general, the encoded GHRH or functional biological equivalent thereof is of formula:

$$-A_{-1}-A_2-DAIFTNSYRKVL-A_3-QLSARKLLQDI-A_4-A_5-RQQGERNQEQGA-OH$$

wherein: $A_1$ is a D-or L-isomer of an amino acid selected from the group consisting of tyrosine ("Y"), or histidine ("H"); $A_2$ is a D-or L-isomer of an amino acid selected from the group consisting of alanine ("A"), valine ("V"), or isoleucine ("I"); $A_3$ is a D-or L-isomer of an amino acid selected from the group consisting of alanine ("A") or glycine ("G"); $A_4$ is a D-or L-isomer of an amino acid selected from the group consisting of methionein ("M"), or leucine ("L"); $A_5$ is a D-or L-isomer of an amino acid selected from the group consisting of serine ("S") or asparagines ("N").

An example of this new optimized synthetic expression vector was denoted as pAV0201 (SEQ ID NO: 2). In order to construct pAV0201 (SEQ ID NO: 2), the unwanted sequences from the pAV0125 (SEQ ID NO: 1) were initially removed. A software program called Vector NTI (version 7.0) was used to generate and match sequences that could be compared and were known to be extraneous (e.g. LacZ promoter). There are many programs such as Vector NTI (version 7.0) that are known in the art and could have been used with similar results to compare and identify specific nucleic acid sequences. Once the extraneous DNA sequences were identified in the pAV0125 plasmid, they were removed by from the plasmid creating a truncated-pAV0125 plasmid. The Gene Forge® optimized synthetic sequences were used to produced codon frequencies that were matched in target and host organisms to ensure proper folding. Gene Forge® was also used to identify and correct a number of deleterious structural elements in the relevant nucleic acid sequences. For example, a bias of GC content can be used to increase mRNA stability or reduce secondary structures; tandem repeat codons or base runs that may impair the gene can be minimized with codon optimization; modification of ribosome binding sites and mRNA degradation sites can be utilized; codon optimization can also reduce or eliminate problem secondary structures within the transcribed mRNA. Although Gene Forge® is a proprietary product of Aptagen that speeds codon optimization analysis, publicly available databases are available that allow a person with average skill in the art to replicate codon optimization protocol.

The pAV0125 plasmid contained a human Growth Hormone poly adenylation region that was approximately 618 bp. The original 618 bp region contained multiple poly adenylation sites and was reduced to only one. As a result over 400 bp were removed to an optimized length of 190 bp (SEQ ID NO: 10). Another 210 bp poly A site is (SEQ ID NO: 16. The origin of replication (SEQ ID NO: 12) was not altered.

A summary of the changes made to the pAV0125 plasmid backbone changes are as follows:

1. Although not wanting to be bound by theory, CpG islands are known to enhance immune responses, and are used to boost immune responses in vaccines (Manders and Thomas, 2000; McCluskie et al., 2000; Scheule, 2000)), the Gene Forge® system can identified and removed as many CpG island as possible without changing the translated amino acid sequence. Additionally, a Nco I site was removed from the Kanamycin sequence without altering the amino acid sequence. Currently the NcoI is an unique site, which makes the plasmid backbone more versatile.
2. The lacZ promoter region that was located downstream of the hGH polyA site was determined to be unnecessary, and it was subsequently removed.
3. A portion of the hGH polyA region was removed to produce a more compact plasmid that is able to accommodate longer DNA fragments or transgenes.
4. A 118 bp portion of the lacZ coding sequence that was located between the KanR gene and the C5-12 synthetic promoter was determined to be unnecessary, and it was subsequently removed.

As a result of the above modifications to the plasmid backbone, a new synthetic plasmid as shown in FIG. 2 was constructed. The pAV0201 optimized plasmid comprises a 2,739 bp circular plasmid (SEQ ID NO: 2). The pAV0201 plasmid contains at least one eukaryotic coding region, and at least one prokaryotic coding sequence, wherein it has been contemplated that the eukaryotic coding region contains a modified growth hormone releasing hormone ("GHRH"). The pAV0201 plasmid also contains a poly A signal, wherein the human growth hormone poly A has been utilized. The pAV0201 plasmid also contains a eukaryotic promoter, and it has been contemplated that the c5-12 synthetic eukaryotic promoter of skeletal actin will be used, although other may be equally useful. The pAV0201 also contains a prokaryotic promoter. The prokaryotic promoter is PNEO, and a 19-47 bp sequence of transposon fragment ("Tn5") with accession number V00618. Additionally one NEO ribosome binding site ("RBS") is present in the pAV0201 plasmid. A complementary origin of replication sequence ("pUC ori") from the pUC18 plasmid (e.g. 685-1466 bp of pUC18). A 5' untranslated region ("5' UTR") was inserted into the pAV0201 plasmid. The 5' UTR is from human growth hormone hGH 5' UTR (i.e. 504-557 bp) accession number M13438.

EXAMPLE 2

Optimized Synthetic GHRH sequences. Another aspect of the current invention is to utilize the above optimized plasmid backbone (pAV0201) and insert codon optimized species specific eukaryotic nucleic acid expression sequences. Although not wanting to limit the scope of the invention, five novel species of optimized GHRH nucleic acid sequences have been inserted into the pAV0201 plasmid backbone using the Nco I and Hind III restriction sites. Each sequence was codon optimized for expression in the corresponding species. The corresponding species in the below examples are as follows: mouse; rat; bovine; ovine; and chicken. The selection of these 5 species is not intended to limit the scope of species specific GHRH insertions into the pAV0201 plasmid backbone. In addition the structural features of pAV0201, each eukaryotic expression sequence also contains a signal peptide sequence for the purpose of making a signal peptide upstream from the mature peptide. Each signal peptide sequence has been contemplated to be the appropriate for the specific species of interest. However, in one example below (e.g. the chicken GHRH sequence), the rat GHRH signal peptide has been utilized. While the natural cDNA sequences (Baird et al., 1986) are known for mouse (Frohman et al., 1989b), rat (Bohlen et al., 1984; Mayo et al., 1985), ovine (Brazeau et al., 1984), bovine (Esch et al., 1983), porcine (Bohlen et al., 1983), chicken (McRory et al., 1997), the codon optimization expression sequences in conjunction with the pAV0201 based plasmid backbone make each of the constructs entirely unique.

Figure 4:
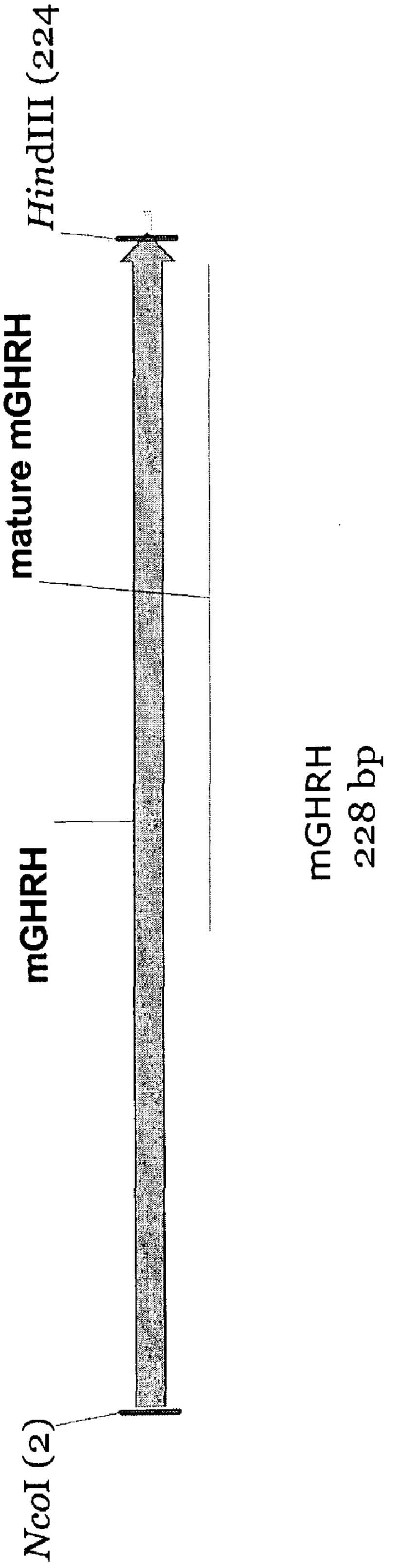
FIG. 4 shows a schematic map of a 228 bp synthetic nucleic acid sequence for mouse GHRH ("mGHRH")

One aspect of the current invention is the insertion of the codon optimized nucleic acid expression sequence for mouse GHRH ("mGHRH") (SEQ ID NO: 5) into the pAV0201 plasmid backbone to give pAV0202 (SEQ ID NO: 17). A schematic representation of the optimized nucleic acid expression sequence for mGHRH is shown in FIG. 4. The optimized 228 bp mGHRH fragment was sub-cloned into the pAV0201 vector using the Nco I and Hind III restriction enzyme cut sites, and standard methods known to one with ordinary skill in the art of molecular biology. FIG. 5 shows a detailed nucleic acid and amino acid sequence of the mGHRH motif, wherein all changes to the nucleic acid expression sequences are labeled in bold. The nucleic acid alignment between the original sequence (GHRH-M Ori) and Gene Forge optimized sequence (GHRH-M Opti) are shown in FIG. 6, changes are labeled in bold. FIG. 7 shows a comparison to indicate that the amino acid sequence has not changed due to codon optimization.

Figure 8:
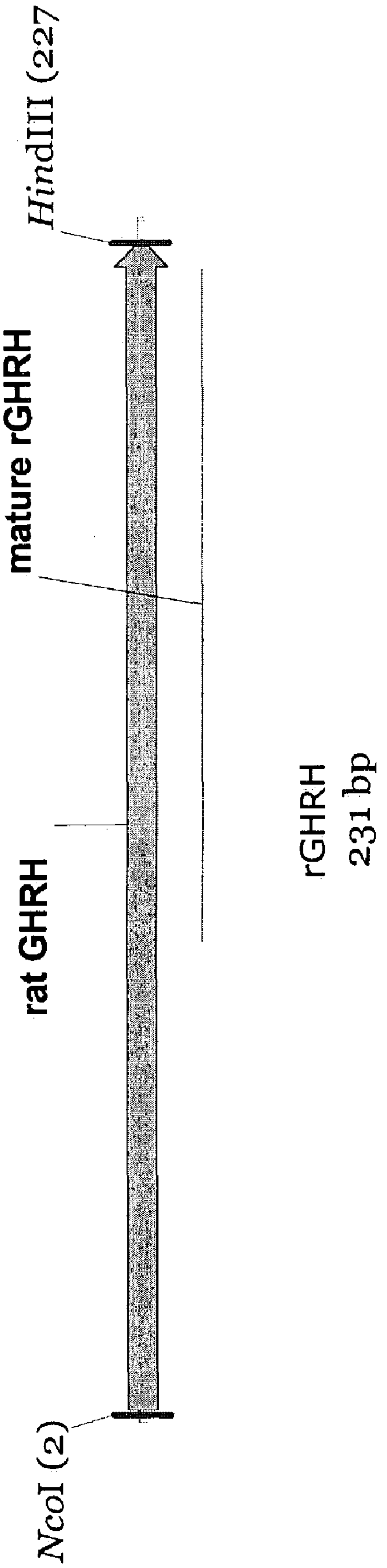
FIG. 8 shows a schematic map of a 231 bp synthetic nucleic acid sequence for rat GHRH ("rGHRH")

Another aspect of the current invention is the insertion of the codon optimized nucleic acid expression sequence for rat GHRH ("rGHRH") (SEQ ID NO: 6) into the pAV0201 plasmid backbone to give pAV0203 (SEQ ID NO: 18). A schematic representation of the optimized nucleic acid expression sequence for rGHRH is shown in FIG. 8. The optimized 231 bp rGHRH fragment was sub-cloned into the pAV0201 vector using the Nco I and Hind III restriction enzyme cut sites, and standard methods known to one with ordinary skill in the art of molecular biology. FIG. 9 shows a detailed nucleic acid and amino acid sequence of the rGHRH motif, wherein all changes to the nucleic acid expression sequences are labeled in bold. The nucleic acid alignment between the original sequence (GHRH-R Ori) and Gene Forge optimized sequence (GHRH-R Opti) are shown in FIG. 10, changes are labeled in bold. FIG. 11 shows a comparison to indicate that the amino acid sequence has not changed due to codon optimization.

Figure 12:
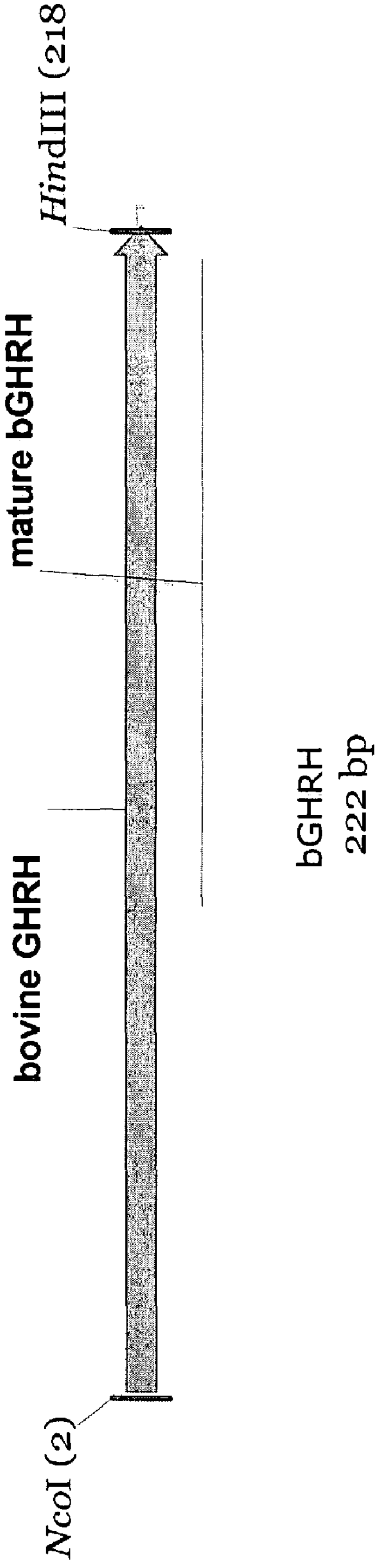
FIG. 12 shows a schematic map of a 222 bp synthetic nucleic acid sequence for bovine GHRH ("bGHRH")

Another aspect of the current invention is the insertion of the codon optimized nucleic acid expression sequence for bovine GHRH ("bGHRH") (SEQ ID NO: 7) into the pAV0201 plasmid backbone to give pAV0204 (SEQ ID NO: 19). A schematic representation of the optimized nucleic acid expression sequence for bGHRH is shown in FIG. 12. The optimized 222 bp bGHRH fragment was sub-cloned into the pAV0201 vector using the Nco I and Hind III restriction enzyme cut sites, and standard methods known to one with ordinary skill in the art of molecular biology. FIG. 13 shows a detailed nucleic acid and amino acid sequence of the bGHRH motif, wherein all changes to the nucleic acid expression sequences are labeled in bold. The nucleic acid alignment between the original sequence (GHRH-B Ori) and Gene Forge optimized sequence (GHRH-B Opti) are shown in FIG. 14, changes are labeled in bold. FIG. 15 shows a comparison to indicate that the amino acid sequence has not changed due to codon optimization.

Figure 16:
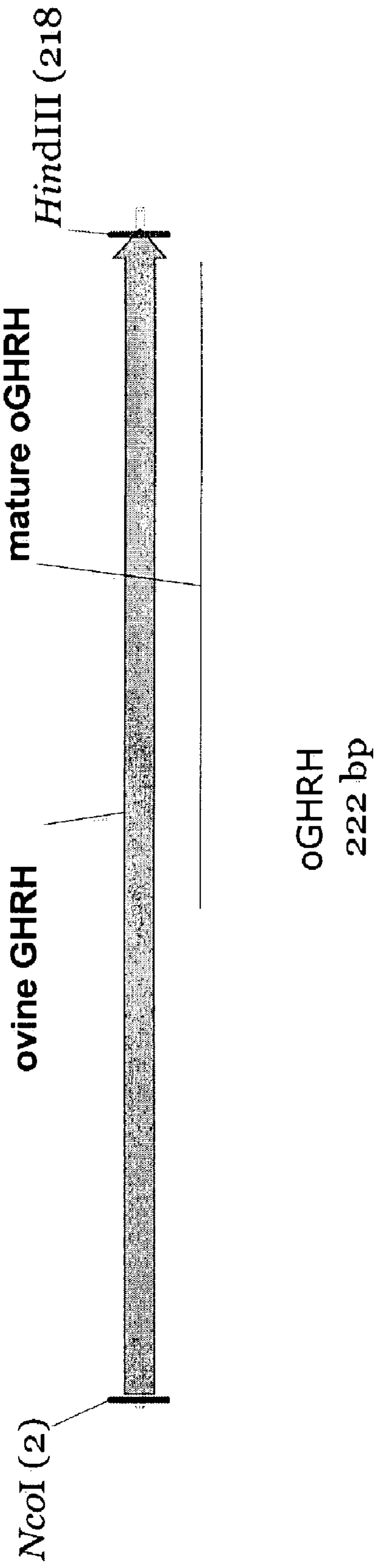
FIG. 16 shows a schematic map of a 222 bp synthetic nucleic acid sequence for bovine GHRH ("oGHRH")

Another aspect of the current invention is the insertion of the codon optimized nucleic acid expression sequence for ovine GHRH ("oGHRH") (SEQ ID NO: 8) into the pAV0201 plasmid backbone to give pAV0205 (SEQ ID NO: 20). A schematic representation of the optimized nucleic acid expression sequence for oGHRH is shown in FIG. 16. The optimized 222 bp oGHRH fragment was sub-cloned into the pAV0201 vector using the Nco I and Hind III restriction enzyme cut sites, and standard methods known to one with ordinary skill in the art of molecular biology. FIG. 17 shows a detailed nucleic acid and amino acid sequence of the oGHRH motif, wherein all changes to the nucleic acid expression sequences are labeled in bold. The nucleic acid alignment between the original sequence (GHRH-O Ori) and Gene Forge optimized sequence (GHRH-O Opti) are shown in FIG. 18, changes are labeled in bold. FIG. 19 shows a comparison to indicate that the amino acid sequence has not changed due to codon optimization.

Figure 20:
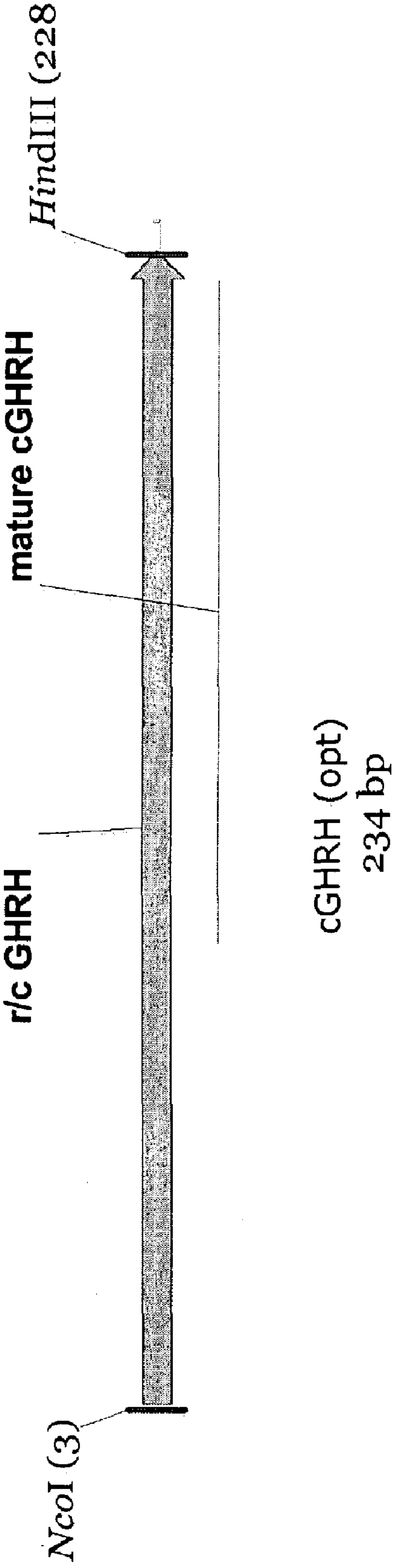
FIG. 20 shows a schematic map of a 234 bp synthetic nucleic acid sequence for chicken GHRH ("cGHRH")

Another aspect of the current invention is the insertion of the codon optimized nucleic acid expression sequence for chicken GHRH ("cGHRH") (SEQ ID NO: 9) into the pAV0201 plasmid backbone to give pAV0206 (SEQ ID NO: 21). A schematic representation of the optimized nucleic acid expression sequence for cGHRH is shown in FIG. 20. The optimized 234 bp cGHRH fragment was sub-cloned into the pAV0201 vector using the Nco I and Hind III restriction enzyme cut sites, and standard methods known to one with ordinary skill in the art of molecular biology. FIG. 21 shows a detailed nucleic acid and amino acid sequence of the cGHRH motif, wherein all changes to the nucleic acid expression sequences are labeled in bold. The nucleic acid alignment between the original sequence (GHRH-C Ori) and Gene Forge optimized sequence (GHRH-C Opti) are shown in FIG. 22, changes are labeled in bold. FIG. 23 shows a comparison to indicate that the amino acid sequence has not changed due to codon optimization. For this particular sequence, the chicken pre-pro hormone signal was replaced with the more compact, shorter rat pre-pro sequence.

The above optimized plasmid constructs can be administered to a mammalian host for various therapeutic effects. One skilled in the art recognizes that different methods of delivery may be utilized to administer an optimized synthetic expression vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome or transporter molecule.

Accordingly, the present invention provides a method of transferring a therapeutic gene to a host, which comprises administering the vector of the present invention, preferably as part of a composition, using any of the aforementioned routes of administration or alternative routes known to those skilled in the art and appropriate for a particular application. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These compositions and methods described herein are by no means all-inclusive, and further methods to suit the specific application will be apparent to the ordinary skilled artisan. Moreover, the effective amount of the compositions can be further approximated through analogy to compounds known to exert the desired effect.

REFERENCES CITED

The entire content of each of the following U.S. patent, foreign patent and publication documents is incorporated by reference herein.

U.S. Patent Documents

U.S. Pat. No. 6,551,996 issued on Apr. 23, 2003 and titled "Super Active Porcine Growth Hormone Releasing Hormone Analog" with Schwartz, et al., listed as inventors.

U.S. Pat. No. 6,114,148 issued on Sep. 5, 2000 and titled "High level expression of proteins" with Seed, et al., listed as inventors.

U.S. Pat. No. 5,292,721 issued on Mar. 8, 1994 and titled "Use of growth hormone to enhance porcine fetal energy and sow lactation performance" with Boyd, et al., listed as inventors.

U.S. Pat. No. 5,134,120 issued on Jul. 28, 1992 and titled "Use of growth hormone to enhance porcine weight gain" with Boyd, et al., listed as inventors.

U.S. Pat. No. 5,061,690 issued on Oct. 29, 1991 and titled "Method for increasing milk production in mammals and/or increasing the birth weight of their newborn and improving postnatal growth" with Kann, et al., listed as inventors.

Publication

Aihara, H. and Miyazaki, J. (1998). Gene transfer into muscle by electroporation in vivo. Nat. Biotechnol. 16, 867-870.

Baird, A., Wehrenberg, W. B., and Ling, N. (1986). Relative potencies of human, rat, bovine/caprine, porcine and ovine hypothalamic growth hormone-releasing factors to release growth hormone by the rat anterior pituitary in vitro. Neuroendocrinology 42, 273-276.

Bercu, B. B., Walker, R. F., (1997). Growth Hormone Secretagogues In Children With Altered Growth. Acta Paediatrica 86, 102-106.

Berneis, K. and Keller, U. (1996). Metabolic actions of growth hormone: direct and indirect. Baillieres Clin. Endocrinol. Metab 10, 337-352.

Blethen, S. L. (1995). Complications of growth hormone therapy in children. Curr. Opin. Pediatr. 7, 466-471.

Blethen, S. L. and Rundle, A. C. (1996). Slipped capital femoral epiphysis in children treated with growth hormone. A summary of the National Cooperative Growth Study experience. Horm. Res. 46, 113-116.

Bohlen, P., Esch, F., Brazeau, P., Ling, N., and Guillemin, R. (1983). Isolation and characterization of the porcine hypothalamic growth hormone releasing factor. Biochem. Biophys. Res. Commun. 116, 726-734.

Bohlen, P., Wehrenberg, W. B., Esch, F., Ling, N., Brazeau, P., and Guillemin, R. (1984). Rat hypothalamic growth hormone-releasing factor: isolation, sequence analysis and total synthesis. Biochemical & Biophysical Research Communications 125, 1005-1012.

Brazeau, P., Bohlen, P., Esch, F., Ling, N., Wehrenberg, W. B., and Guillemin, R. (1984). Growth hormone-releasing factor from ovine and caprine hypothalamus: isolation, sequence analysis and total synthesis. Biochemical & Biophysical Research Communications 125, 606-614.

Burgert, T. S., Vuguin, P. M., DiMartino-Nardi, J., Attie, K. M., and Saenger, P. (2002). Assessing insulin resistance: application of a fasting glucose to insulin ratio in growth hormone-treated children. Horm. Res. 57, 37-42.

Carrel, A. L. and Allen, D. B. (2000). Effects of growth hormone on body composition and bone metabolism. Endocrine. 12, 163-172.

Corpas, E., Harman, S. M., and Blackman, M. R. (1993a). Human growth hormone and human aging. [Review]. Endocrine Reviews 14, 20-39.

Corpas, E., Harman, S. M., Pineyro, M. A., Roberson, R., and Blackman, M. R. (1993b). Continuous subcutaneous infusions of growth hormone (GH) releasing hormone 1-44 for 14 days increase GH and insulin-like growth factor-I levels in old men. Journal of Clinical Endocrinology & Metabolism 76, 134-138.

Cuttler, L. (1996). The regulation of growth hormone secretion. Endocrinol. Metab Clin. North Am. 25, 541-571.

Danko, I. and Wolff, J. A. (1994). Direct gene transfer into muscle. [Review]. Vaccine 12, 1499-1502.

Darquet, A. M., Cameron, B., Wils, P., Scherman, D., and Crouzet, J. (1997). A new DNA vehicle for nonviral gene delivery: supercoiled minicircle. Gene Ther. 4, 1341-1349.

Darquet, A. M., Rangara, R., Kreiss, P., Schwartz, B., Naimi, S., Delaere, P., Crouzet, J., and Scherman, D. (1999). Minicircle: an improved DNA molecule for in vitro and in vivo gene transfer. Gene Ther. 6, 209-218.

Draghia-Akli, R., Fiorotto, M. L., Hill, L. A., Malone, P. B., Deaver, D. R., and Schwartz, R. J. (1999). Myogenic expression of an injectable protease-resistant growth hormone-releasing hormone augments long-term growth in pigs. Nat. Biotechnol. 17, 1179-1183.

Draghia-Akli, R., Li, X. G., Schwartz, R. J. (1997). Enhanced Growth By Ectopic Expression Of Growth Hormone Releasing Hormone Using An Injectable Myogenic Vector. nature biotechnology 15, 1285-1289.

Draghia-Akli, R., Malone, P. B., Hill, L. A., Ellis, K. M., Schwartz, R. J., and Nordstrom, J. L. (2002). Enhanced animal growth via ligand-regulated GHRH myogenic-injectable vectors. FASEB J. 16, 426-428.

Duck, S. C., Schwarz, H. P., Costin, G., Rapaport, R., Arslanian, S., Hayek, A., Connors, M., and Jaramillo, J. (1992). Subcutaneous growth hormone-releasing hormone therapy in growth hormone-deficient children: first year of therapy. Journal of Clinical Endocrinology & Metabolism 75, 1115-1120.

Esch, F., Bohlen, P., Ling, N., Brazeau, P., and Guillemin, R. (1983). Isolation and characterization of the bovine hypothalamic growth hormone releasing factor. Biochemical & Biophysical Research Communications 117, 772-779.

Evans, W. S., Vance, M. L., Kaiser, D. L., Sellers, R. P., Borges, J. L., Downs, T. R., Frohman, L. A., Rivier, J., Vale, W., and Thomer, M. O. (1985). Effects of intravenous, subcutaneous, and intranasal administration of growth hormone (GH)-releasing hormone-40 on serum GH concentrations in normal men. Journal of Clinical Endocrinology & Metabolism 61, 846-850.

Faglia, G., Arosio, M., and Bazzoni, N. (1992). Ectopic acromegaly. [Review]. Endocrinology & Metabolism Clinics of North America 21, 575-595.

Frohman, L. A., Downs, T. R., and Chomczynski, P. (1992). Regulation of growth hormone secretion. [Review]. Frontiers in Neuroendocrinology 13, 344-405.

Frohman, L. A., Downs, T. R., Heimer, E. P., and Felix, A. M. (1989a). Dipeptidylpeptidase IV and trypsin-like enzymatic degradation of human growth hormone-releasing hormone in plasma. J. Clin. Invest. 83, 1533-1540.

Frohman, L. A., Downs, T. R., Williams, T. C., Heimer, E. P., Pan, Y. C., and Felix, A. M. (1986). Rapid enzymatic degradation of growth hormone-releasing hormone by plasma in vitro and in vivo to a biologically inactive product cleaved at the $NH_2$ terminus. J. Clin. Invest. 78, 906-913.

Frohman, M. A., Downs, T. R., Chomczynski, P., and Frohman, L. A. (1989b). Cloning and characterization of mouse growth hormone-releasing hormone (GRH) complementary DNA: increased GRH messenger RNA levels in the growth hormone-deficient lit/lit mouse. Mol. Endocrinol. 3, 1529-1536.

Geffner, M. (1997). Effects of growth hormone and insulin-like growth factor I. Acta Paediatr. Suppl 423, 76-79.

Hart, D. W., Hemdon, D. N., Klein, G., Lee, S. B., Celis, M., Mohan, S., Chinkes, D. L., and Wolf, S. E. (2001). Attenuation of posttraumatic muscle catabolism and osteopenia by long-term growth hormone therapy. Ann. Surg. 233, 827-834.

Kotzmann, H., Yilmaz, N., Lercher, P., Riedl, M., Schmidt, A., Schuster, E., Kreuzer, S., Geyer, G., Frisch, H., Horl, W. H., Mayer, G., and Luger, A. (2001). Differential effects of growth hormone therapy in malnourished hemodialysis patients. Kidney Int. 60, 1578-1585.

Lal, S. O., Wolf, S. E., and Herndon, D. N. (2000). Growth hormone, burns and tissue healing. Growth Horm. IGF. Res. 10 Suppl B:S39-43., S39-S43.

LeRoith, D., Yanowski, J., Kaldjian, E. P., Jaffe, E. S., LeRoith, T., Purdue, K., Cooper, B. D., Pyle, R., and Adler, W. (1996). The effects of growth hormone and insulin-like growth factor I on the immune system of aged female monkeys. Endocrinology 137, 1071-1079.

Lesbordes, J. C., Bordet, T., Haase, G., Castelnau-Ptakhine, L., Rouhani, S., Gilgenkrantz, H., and Kahn, A. (2002). In vivo electrotransfer of the cardiotrophin-1 gene into skeletal muscle slows down progression of motor neuron degeneration in pmn mice. Hum. Mol. Genet. 11, 1615-1625.

Manders, P. and Thomas, R. (2000). Immunology of DNA vaccines: CpG motifs and antigen presentation. Inflamm. Res. 49, 199-205.

Mayo, K. E., Cerelli, G. M., Rosenfeld, M. G., and Evans, R. M. (1985). Characterization of cDNA and genomic clones encoding the precursor to rat hypothalamic growth hormone-releasing factor. Nature 314, 464-467.

McCluskie, M. J., Weeratna, R. D., and Davis, H. L. (2000). The role of CpG in DNA vaccines. Springer Semin. Immunopathol. 22, 125-132.

McRory, J. E., Parker, R. L., and Sherwood, N. M. (1997). Expression and alternative processing of a chicken gene encoding both growth hormone-releasing hormone and pituitary adenylate cyclase-activating polypeptide. DNA Cell Biol. 16, 95-102.

Melmed, S. (1991). Extrapituitary Acromegaly. [Review]. Endocrinology & Metabolism Clinics of North America 20, 507-518.

Mulligan, K., Tai, V. W., and Schambelan, M. (1999). Use of growth hormone and other anabolic agents in AIDS wasting. JPEN J. Parenter. Enteral Nutr. 23, S202-S209.

Narum, D. L., Kumar, S., Rogers, W. O., Fuhrmann, S. R., Liang, H., Oakley, M., Taye, A., Sim, B. K., and Hoffman, S. L. (2001). Codon optimization of gene fragments encoding Plasmodium falciparum merzoite proteins enhances DNA vaccine protein expression and immunogenicity in mice. Infect. Immun. 69, 7250-7253.

Scheule, R. K. (2000). The role of CpG motifs in immunostimulation and gene therapy. Adv. Drug Deliv. Rev. 44,119-134.

Shi, H., Yan, P. S., Chen, C. M., Rahmatpanah, F., Lofton-Day, C., Caldwell, C. W., and Huang, T. H. (2002). Expressed CpG island sequence tag microarray for dual screening of DNA hypermethylation and gene silencing in cancer cells. Cancer Res. 62, 3214-3220.

Shiraishi, M., Sekiguchi, A., Terry, M. J., Oates, A. J., Miyamoto, Y., Chuu, Y. H., Munakata, M., and Sekiya, T. (2002). A comprehensive catalog of CpG islands methylated in human lung adenocarcinomas for the identification of tumor suppressor genes. Oncogene 21, 3804-3813.

Soubrier, F., Cameron, B., Manse, B., Somarriba, S., Dubertret, C., Jaslin, G., Jung, G., Caer, C. L., Dang, D., Mouvault, J. M., Scherman, D., Mayaux, J. F., and Crouzet, J. (1999). pCOR: a new design of plasmid vectors for nonviral gene therapy. Gene Ther. 6, 1482-1488.

Wolff, J. A., Ludtke, J. J., Acsadi, G., Williams, P., and Jani, A. (1992). Long-term persistence of plasmid DNA and foreign gene expression in mouse muscle. Human Molecular Genetics 1, 363-369.

What is claimed is:

1. A synthetic mammalian expression plasmid for plasmid mediated gene supplementation in a species comprising:

(a) a synthetic or eukaryotic promoter comprising SEQ ID NO: 15;

(b) a codon-optimized eukaryotic therapeutic gene sequence comprising SEQ ID NO: 7;

(c) a polyadenylation signal;

(d) a selectable marker gene sequence;

(e) a ribosomal binding site;

(f) a promoter for the selectable marker gene sequence; and (g) an origin of replication;

wherein the synthetic or eukaryotic promoter, the codon-optimized-eukaryotic therapeutic gene sequence, and the polyadenylation signal comprise therapeutic elements of the synthetic mammalian expression plasmid; the therapeutic elements are operatively linked and located in a first operatively-linked arrangement; the selectable marker gene promoter, the ribosomal binding site, the selectable marker gene sequence, and the origin of replication comprise replication elements of the synthetic mammalian expression plasmid; the replication elements are operatively linked and located in a second-operatively-linked arrangement; and the first-operatively linked arrangement and the second-operatively-linked arrangement comprise a circular structure of the synthetic mammalian expression plasmid.

2. A synthetic mammalian expression plasmid comprising SEQ ID NO: 19.

* * * * *

SEQUENCE LISTING

```
<160> NUMBER OF SEQ ID NOS: 21

<210> SEQ ID NO 1
<211> LENGTH: 3534
<212> TYPE: DNA
<213> ORGANISM: artificial sequence
<220> FEATURE:
<223> OTHER INFORMATION: Plasmid vector having an analog GHRH sequence.

<400> SEQUENCE: 1

gttgtaaaac gacggccagt gaattgtaat acgactcact atagggcgaa ttggagctcc     60

accgcggtgg cggccgtccg ccctcggcac catcctcacg acacccaaat atggcgacgg    120

gtgaggaatg gtggggagtt atttttagag cggtgaggaa ggtgggcagg cagcaggtgt    180

tggcgctcta aaaataactc ccgggagtta tttttagagc ggaggaatgg tggacaccca    240

aatatggcga cggttcctca cccgtcgcca tatttgggtg tccgccctcg gccggggccg    300

cattcctggg ggccgggcgg tgctcccgcc cgcctcgata aaaggctccg gggccggcgg    360

cggcccacga gctacccgga ggagcgggag gcgccaagct ctagaactag tggatcccaa    420

ggcccaactc cccgaaccac tcagggtcct gtggacagct cacctagctg ccatggtgct    480

ctgggtgttc ttctttgtga tcctcaccct cagcaacagc tcccactgct ccccacctcc    540

ccctttgacc ctcaggatgc ggcggcacgt agatgccatc ttcaccaaca gctaccggaa    600

ggtgctggcc cagctgtccg cccgcaagct gctccaggac atcctgaaca ggcagcaggg    660
```

-continued

```
agagaggaac caagagcaag gagcataatg actgcaggaa ttcgatatca agcttatcgg    720
ggtggcatcc ctgtgacccc tccccagtgc ctctcctggc cctggaagtt gccactccag    780
tgcccaccag ccttgtccta ataaaattaa gttgcatcat tttgtctgac taggtgtcct    840
tctataatat tatggggtgg aggggggtgg tatggagcaa ggggcaagtt gggaagacaa    900
cctgtagggc ctgcggggtc tattgggaac caagctggag tgcagtggca caatcttggc    960
tcactgcaat ctccgcctcc tgggttcaag cgattctcct gcctcagcct cccgagttgt   1020
tgggattcca ggcatgcatg accaggctca gctaattttt gtttttttgg tagagacggg   1080
gtttcaccat attggccagg ctggtctcca actcctaatc tcaggtgatc tacccacctt   1140
ggcctcccaa attgctggga ttacaggcgt gaaccactgc tcccttccct gtccttctga   1200
ttttaaaata actataccag caggaggacg tccagacaca gcataggcta cctggccatg   1260
cccaaccggt gggacatttg agttgcttgc ttggcactgt cctctcatgc gttgggtcca   1320
ctcagtagat gcctgttgaa ttcgataccg tcgacctcga ggggggggcc ggtaccagct   1380
tttgttccct ttagtgaggg ttaatttcga gcttggcgta atcatggtca tagctgtttc   1440
ctgtgtgaaa ttgttatccg ctcacaattc cacacaacat acgagccgga agcataaagt   1500
gtaaagcctg gggtgcctaa tgagtgagct aactcacatt aattgcgttg cgctcactgc   1560
ccgctttcca gtcgggaaac ctgtcgtgcc agctgcatta atgaatcggc caacgcgcgg   1620
ggagaggcgg tttgcgtatt gggcgctctt ccgcttcctc gctcactgac tcgctgcgct   1680
cggtcgttcg gctgcggcga gcggtatcag ctcactcaaa ggcggtaata cggttatcca   1740
cagaatcagg ggataacgca ggaaagaaca tgtgagcaaa aggccagcaa aaggccagga   1800
accgtaaaaa ggccgcgttg ctggcgtttt tccataggct ccgcccccct gacgagcatc   1860
acaaaaatcg acgctcaagt cagaggtggc gaaacccgac aggactataa agataccagg   1920
cgtttccccc tggaagctcc ctcgtgcgct ctcctgttcc gaccctgccg cttaccggat   1980
acctgtccgc ctttctccct tcgggaagcg tggcgctttc tcatagctca cgctgtaggt   2040
atctcagttc ggtgtaggtc gttcgctcca agctgggctg tgtgcacgaa ccccccgttc   2100
agcccgaccg ctgcgcctta tccggtaact atcgtcttga gtccaacccg gtaagacacg   2160
acttatcgcc actggcagca gccactggta acaggattag cagagcgagg tatgtaggcg   2220
gtgctacaga gttcttgaag tggtggccta actacggcta cactagaaga acagtatttg   2280
gtatctgcgc tctgctgaag ccagttacct tcggaaaaag agttggtagc tcttgatccg   2340
gcaaacaaac caccgctggt agcggtggtt tttttgtttg caagcagcag attacgcgca   2400
gaaaaaaagg atctcaagaa gatcctttga tcttttctac ggggtctgac gctcagaaga   2460
actcgtcaag aaggcgatag aaggcgatgc gctgcgaatc gggagcggcg ataccgtaaa   2520
gcacgaggaa gcggtcagcc cattcgccgc caagctcttc agcaatatca cgggtagcca   2580
acgctatgtc ctgatagcgg tccgccacac ccagccggcc acagtcgatg aatccagaaa   2640
agcggccatt ttccaccatg atattcggca agcaggcatc gccatgggtc acgacgagat   2700
cctcgccgtc gggcatgcgc gccttgagcc tggcgaacag ttcggctggc gcgagcccct   2760
gatgctcttc gtccagatca tcctgatcga caagaccggc ttccatccga gtacgtgctc   2820
gctcgatgcg atgtttcgct tggtggtcga atgggcaggt agccggatca agcgtatgca   2880
gccgccgcat tgcatcagcc atgatggata ctttctcggc aggagcaagg tgagatgaca   2940
ggagatcctg ccccggcact tcgcccaata gcagccagtc ccttcccgct tcagtgacaa   3000
```

-continued

```
cgtcgagcac agctgcgcaa ggaacgcccg tcgtggccag ccacgatagc cgcgctgcct   3060

cgtcctgcag ttcattcagg gcaccggaca ggtcggtctt gacaaaaaga accgggcgcc   3120

cctgcgctga cagccggaac acggcggcat cagagcagcc gattgtctgt tgtgcccagt   3180

catagccgaa tagcctctcc acccaagcgg ccggagaacc tgcgtgcaat ccatcttgtt   3240

caatcatgcg aaacgatcct catcctgtct cttgatcaga tcttgatccc ctgcgccatc   3300

agatccttgg cggcaagaaa gccatccagt ttactttgca gggcttccca accttaccag   3360

agggcgcccc agctggcaat tccggttcgc ttgctgtcca taaaaccgcc cagtctagca   3420

actgttggga agggcgatcg gtgcgggcct cttcgctatt acgccagctg gcgaaagggg   3480

gatgtgctgc aaggcgatta agttgggtaa cgccagggtt ttcccagtca cgac         3534
```

<210> SEQ ID NO 2
<211> LENGTH: 2739
<212> TYPE: DNA
<213> ORGANISM: artificial sequence
<220> FEATURE:
<223> OTHER INFORMATION: Plasmid vector having an analog GHRH sequence.

<400> SEQUENCE: 2

```
ccaccgcggt ggcggccgtc cgccctcggc accatcctca cgacacccaa atatggcgac     60

gggtgaggaa tggtggggag ttatttttag agcggtgagg aaggtgggca ggcagcaggt    120

gttggcgctc taaaaataac tcccgggagt tatttttaga gcggaggaat ggtggacacc    180

caaatatggc gacggttcct cacccgtcgc catatttggg tgtccgccct cggccggggc    240

cgcattcctg ggggccgggc ggtgctcccg cccgcctcga taaaaggctc cggggccggc    300

ggcggcccac gagctacccg gaggagcggg aggcgccaag cggatcccaa ggcccaactc    360

cccgaaccac tcagggtcct gtggacagct cacctagctg ccatggtgct ctgggtgttc    420

ttctttgtga tcctcaccct cagcaacagc tcccactgct ccccacctcc ccctttgacc    480

ctcaggatgc ggcggtatgc agatgccatc ttcaccaaca gctaccggaa ggtgctgggc    540

cagctgtccg cccgcaagct gctccaggac atcatgagca ggcagcaggg agagaggaac    600

caagagcaag gagcataatg actgcaggaa ttcgatatca agcttatcgg ggtggcatcc    660

ctgtgacccc tccccagtgc ctctcctggc cctggaagtt gccactccag tgcccaccag    720

ccttgtccta ataaaattaa gttgcatcat tttgtctgac taggtgtcct tctataatat    780

tatggggtgg aggggggtgg tatggagcaa ggggcaagtt gggaagacaa cctgtagggc    840

tcgagggggg gcccggtacc agcttttgtt ccctttagtg agggttaatt tcgagcttgg    900

tcttccgctt cctcgctcac tgactcgctg cgctcggtcg ttcggctgcg gcgagcggta    960

tcagctcact caaaggcggt aatacggtta tccacagaat caggggataa cgcaggaaag   1020

aacatgtgag caaaaggcca gcaaaaggcc aggaaccgta aaaaggccgc gttgctggcg   1080

tttttccata ggctccgccc ccctgacgag catcacaaaa atcgacgctc aagtcagagg   1140

tggcgaaacc cgacaggact ataaagatac caggcgtttc cccctggaag ctccctcgtg   1200

cgctctcctg ttccgaccct gccgcttacc ggatacctgt ccgcctttct cccttcggga   1260

agcgtggcgc tttctcatag ctcacgctgt aggtatctca gttcggtgta ggtcgttcgc   1320

tccaagctgg gctgtgtgca cgaacccccc gttcagcccg accgctgcgc cttatccggt   1380

aactatcgtc ttgagtccaa cccggtaaga cacgacttat cgccactggc agcagccact   1440

ggtaacagga ttagcagagc gaggtatgta ggcggtgcta cagagttctt gaagtggtgg   1500

cctaactacg gctacactag aagaacagta tttggtatct gcgctctgct gaagccagtt   1560
```

-continued

```
accttcggaa aaagagttgg tagctcttga tccggcaaac aaaccaccgc tggtagcggt   1620
ggtttttttg tttgcaagca gcagattacg cgcagaaaaa aaggatctca agaagatcct   1680
ttgatctttt ctacggggtc tgacgctcag ctagcgctca gaagaactcg tcaagaaggc   1740
gatagaaggc gatgcgctgc gaatcgggag cggcgatacc gtaaagcacg aggaagcggt   1800
cagcccattc gccgccaagc tcttcagcaa tatcacgggt agccaacgct atgtcctgat   1860
agcggtccgc cacacccagc cggccacagt cgatgaatcc agaaaagcgg ccattttcca   1920
ccatgatatt cggcaagcag gcatcgccat gagtcacgac gagatcctcg ccgtcgggca   1980
tgcgcgcctt gagcctggcg aacagttcgg ctggcgcgag cccctgatgc tcttcgtcca   2040
gatcatcctg atcgacaaga ccggcttcca tccgagtacg tgctcgctcg atgcgatgtt   2100
tcgcttggtg gtcgaatggg caggtagccg gatcaagcgt atgcagccgc cgcattgcat   2160
cagccatgat ggatactttc tcggcaggag caaggtgaga tgacaggaga tcctgccccg   2220
gcacttcgcc caatagcagc cagtcccttc ccgcttcagt gacaacgtcg agcacagctg   2280
cgcaaggaac gcccgtcgtg gccagccacg atagccgcgc tgcctcgtcc tgcagttcat   2340
tcagggcacc ggacaggtcg gtcttgacaa aaagaaccgg gcgcccctgc gctgacagcc   2400
ggaacacggc ggcatcagag cagccgattg tctgttgtgc ccagtcatag ccgaatagcc   2460
tctccaccca agcggccgga gaacctgcgt gcaatccatc ttgttcaatc atgcgaaacg   2520
atcctcatcc tgtctcttga tcagatcttg atcccctgcg ccatcagatc cttggcggca   2580
agaaagccat ccagtttact ttgcagggct tcccaacctt accagagggc gccccagctg   2640
gcaattccgg ttcgcttgct gtccataaaa ccgcccagtc tagcaactgt tgggaagggc   2700
gatcgtgtaa tacgactcac tatagggcga attggagct                          2739
```

<210> SEQ ID NO 3
<211> LENGTH: 795
<212> TYPE: DNA
<213> ORGANISM: artificial sequence
<220> FEATURE:
<223> OTHER INFORMATION: Coding sequence having an antibiotic resistance gene Kanamycin.

<400> SEQUENCE: 3

```
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
caggacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac tcatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                     795
```

-continued

<210> SEQ ID NO 4
<211> LENGTH: 219
<212> TYPE: DNA
<213> ORGANISM: artificial sequence
<220> FEATURE:
<223> OTHER INFORMATION: Sequence for an analog porcine GHRH sequence.

<400> SEQUENCE: 4
atggtgctct gggtgttctt ctttgtgatc ctcaccctca gcaacagctc ccactgctcc 60
ccacctcccc ctttgaccct caggatgcgg cggcacgtag atgccatctt caccaacagc 120
taccggaagg tgctggccca gctgtccgcc cgcaagctgc tccaggacat cctgaacagg 180
cagcagggag agaggaacca agagcaagga gcataatga 219

<210> SEQ ID NO 5
<211> LENGTH: 246
<212> TYPE: DNA
<213> ORGANISM: artificial sequence
<220> FEATURE:
<223> OTHER INFORMATION: Sequence for an analog mouse GHRH sequence.

<400> SEQUENCE: 5
gccatggtgc tctgggtgct ctttgtgatc ctcatcctca ccagcggcag ccactgcagc 60
ctgcctccca gccctccctt caggatgcag aggcacgtgg acgccatctt caccaccaac 120
tacaggaagc tgctgagcca gctgtacgcc aggaaggtga tccaggacat catgaacaag 180
cagggcgaga ggatccagga gcagagggcc aggctgagct gataagcttg cgatgagttc 240
ttctaa 246

<210> SEQ ID NO 6
<211> LENGTH: 234
<212> TYPE: DNA
<213> ORGANISM: artificial sequence
<220> FEATURE:
<223> OTHER INFORMATION: Sequence for an analog porcine GHRH sequence.

<400> SEQUENCE: 6
gccatggccc tgtgggtgtt cttcgtgctg ctgaccctga ccagcggaag ccactgcagc 60
ctgcctccca gccctccctt cagggtgcgc cggcacgccg acgccatctt caccagcagc 120
tacaggagga tcctgggcca gctgtacgct aggaagctcc tgcacgagat catgaacagg 180
cagcagggcg agaggaacca ggagcagagg agcaggttca actgataagc ttgc 234

<210> SEQ ID NO 7
<211> LENGTH: 225
<212> TYPE: DNA
<213> ORGANISM: artificial sequence
<220> FEATURE:
<223> OTHER INFORMATION: Sequence for an analog bovine GHRH sequence.

<400> SEQUENCE: 7
gccatggtgc tgtgggtgtt cttcctggtg accctgaccc tgagcagcgg ctcccacggc 60
tccctgccct cccagcctct gcgcatccct cgctacgccg acgccatctt caccaacagc 120
taccgcaagg tgctcggcca gctcagcgcc cgcaagctcc tgcaggacat catgaaccgg 180
cagcagggcg agcgcaacca ggagcaggga gcctgataag cttgc 225

<210> SEQ ID NO 8
<211> LENGTH: 225
<212> TYPE: DNA

-continued

```
<213> ORGANISM: artificial sequence
<220> FEATURE:
<223> OTHER INFORMATION: Sequence for an analog ovine GHRH sequence.

<400> SEQUENCE: 8

gccatggtgc tgtgggtgtt cttcctggtg accctgaccc tgagcagcgg aagccacggc     60

agcctgccca gccagcccct gaggatccct aggtacgccg acgccatctt caccaacagc    120

tacaggaaga tcctgggcca gctgagcgct aggaagctcc tgcaggacat catgaacagg    180

cagcagggcg agaggaacca ggagcagggc gcctgataag cttgc                    225


<210> SEQ ID NO 9
<211> LENGTH: 246
<212> TYPE: DNA
<213> ORGANISM: artificial sequence
<220> FEATURE:
<223> OTHER INFORMATION: Sequence for an analog chicken GHRH sequence.

<400> SEQUENCE: 9

gccatggtgc tctgggtgct ctttgtgatc ctcatcctca ccagcggcag ccactgcagc     60

ctgcctccca gccctccctt caggatgcag aggcacgtgg acgccatctt caccaccaac    120

tacaggaagc tgctgagcca gctgtacgcc aggaaggtga tccaggacat catgaacaag    180

cagggcgaga ggatccagga gcagagggcc aggctgagct gataagcttg cgatgagttc    240

ttctaa                                                               246


<210> SEQ ID NO 10
<211> LENGTH: 190
<212> TYPE: DNA
<213> ORGANISM: artificial sequence
<220> FEATURE:
<223> OTHER INFORMATION: Nucleic acid sequence of  human growth hormone
      poly A tail.

<400> SEQUENCE: 10

gggtggcatc cctgtgaccc ctccccagtg cctctcctgg ccctggaagt tgccactcca     60

gtgcccacca gccttgtcct aataaaatta agttgcatca ttttgtctga ctaggtgtcc    120

ttctataata ttatggggtg gaggggggtg gtatggagca aggggcaagt tgggaagaca    180

acctgtaggg                                                           190


<210> SEQ ID NO 11
<211> LENGTH: 55
<212> TYPE: DNA
<213> ORGANISM: artificial sequence
<220> FEATURE:
<223> OTHER INFORMATION: Nucleic acid sequence of human growth hormone
      5' untranslated region

<400> SEQUENCE: 11

caaggcccaa ctccccgaac cactcagggt cctgtggaca gctcacctag ctgcc          55


<210> SEQ ID NO 12
<211> LENGTH: 782
<212> TYPE: DNA
<213> ORGANISM: artificial sequence
<220> FEATURE:
<223> OTHER INFORMATION: Nucleic acid sequence of a plasmid pUC-18
      origin of replicaiton

<400> SEQUENCE: 12

tcttccgctt cctcgctcac tgactcgctg cgctcggtcg ttcggctgcg gcgagcggta     60
```

-continued

```
tcagctcact caaaggcggt aatacggtta tccacagaat caggggataa cgcaggaaag    120

aacatgtgag caaaaggcca gcaaaaggcc aggaaccgta aaaaggccgc gttgctggcg    180

tttttccata ggctccgccc ccctgacgag catcacaaaa atcgacgctc aagtcagagg    240

tggcgaaacc cgacaggact ataaagatac caggcgtttc cccctggaag ctccctcgtg    300

cgctctcctg ttccgaccct gccgcttacc ggatacctgt ccgcctttct cccttcggga    360

agcgtggcgc tttctcatag ctcacgctgt aggtatctca gttcggtgta ggtcgttcgc    420

tccaagctgg gctgtgtgca cgaacccccc gttcagcccg accgctgcgc cttatccggt    480

aactatcgtc ttgagtccaa cccggtaaga cacgacttat cgccactggc agcagccact    540

ggtaacagga ttagcagagc gaggtatgta ggcggtgcta cagagttctt gaagtggtgg    600

cctaactacg gctacactag aaggacagta tttggtatct gcgctctgct gaagccagtt    660

accttcggaa aaagagttgg tagctcttga tccggcaaac aaaccaccgc tggtagcggt    720

ggtttttttg tttgcaagca gcagattacg cgcagaaaaa aaggatctca agaagatcct    780

tt                                                                   782


<210> SEQ ID NO 13
<211> LENGTH: 5
<212> TYPE: DNA
<213> ORGANISM: artificial sequence
<220> FEATURE:
<223> OTHER INFORMATION: This is a NEO ribosomal binding site

<400> SEQUENCE: 13

tcctc                                                                  5


<210> SEQ ID NO 14
<211> LENGTH: 29
<212> TYPE: DNA
<213> ORGANISM: artificial sequence
<220> FEATURE:
<223> OTHER INFORMATION: Nucleic acid sequence of a prokaryotic PNEO
      promoter.

<400> SEQUENCE: 14

accttaccag agggcgcccc agctggcaa                                       29


<210> SEQ ID NO 15
<211> LENGTH: 323
<212> TYPE: DNA
<213> ORGANISM: artificial sequence
<220> FEATURE:
<223> OTHER INFORMATION: Nucleic acid sequence of a eukaryotic promoter
      c5-12.

<400> SEQUENCE: 15

cggccgtccg ccctcggcac catcctcacg acacccaaat atggcgacgg gtgaggaatg     60

gtggggagtt atttttagag cggtgaggaa ggtgggcagg cagcaggtgt tggcgctcta    120

aaaataactc ccgggagtta tttttagagc ggaggaatgg tggacaccca aatatggcga    180

cggttcctca cccgtcgcca tatttgggtg tccgccctcg gccggggccg cattcctggg    240

ggccgggcgg tgctcccgcc cgcctcgata aaaggctccg gggccggcgg cggcccacga    300

gctacccgga ggagcgggag gcg                                            323


<210> SEQ ID NO 16
<211> LENGTH: 210
<212> TYPE: DNA
<213> ORGANISM: artificial sequence
```

-continued

<220> FEATURE:
<223> OTHER INFORMATION: Optimized nucleic acid sequence of a human
growth hormone poly A tail

<400> SEQUENCE: 16
ttatcggggt ggcatccctg tgacccctcc ccagtgcctc tcctggccct ggaagttgcc 60
actccagtgc ccaccagcct tgtcctaata aaattaagtt gcatcatttt gtctgactag 120
gtgtccttct ataatattat ggggtggagg ggggtggtat ggagcaaggg gcaagttggg 180
aagacaacct gtagggctcg agggggggcc 210

<210> SEQ ID NO 17
<211> LENGTH: 2722
<212> TYPE: DNA
<213> ORGANISM: artificial sequence
<220> FEATURE:
<223> OTHER INFORMATION: Plasmid vector having a codon optimized mouse
GHRH sequence

<400> SEQUENCE: 17
ccaccgcggt ggcggccgtc cgccctcggc accatcctca cgacacccaa atatggcgac 60
gggtgaggaa tggtggggag ttatttttag agcggtgagg aaggtgggca ggcagcaggt 120
gttggcgctc taaaaataac tcccgggagt tatttttaga gcggaggaat ggtggacacc 180
caaatatggc gacggttcct cacccgtcgc catatttggg tgtccgccct cggccggggc 240
cgcattcctg ggggccgggc ggtgctcccg cccgcctcga taaaaggctc cggggccggc 300
ggcggcccac gagctacccg gaggagcggg aggcgccaag cggatcccaa ggcccaactc 360
cccgaaccac tcagggtcct gtggacagct cacctagctg ccatggtgct ctgggtgctc 420
tttgtgatcc tcatcctcac cagcggcagc cactgcagcc tgcctcccag ccctcccttc 480
aggatgcaga ggcacgtgga cgccatcttc accaccaact acaggaagct gctgagccag 540
ctgtacgcca ggaaggtgat ccaggacatc atgaacaagc agggcgagag gatccaggag 600
cagagggcca ggctgagctg ataagcttat cggggtggca tccctgtgac ccctccccag 660
tgcctctcct ggccctggaa gttgccactc cagtgcccac cagccttgtc ctaataaaat 720
taagttgcat cattttgtct gactaggtgt ccttctataa tattatgggg tggagggggg 780
tggtatggag caaggggcaa gttgggaaga caacctgtag ggctcgaggg ggggcccggt 840
accagctttt gttcccttta gtgagggtta atttcgagct tggtcttccg cttcctcgct 900
cactgactcg ctgcgctcgg tcgttcggct gcggcgagcg gtatcagctc actcaaaggc 960
ggtaatacgg ttatccacag aatcagggga taacgcagga aagaacatgt gagcaaaagg 1020
ccagcaaaag gccaggaacc gtaaaaaggc cgcgttgctg gcgtttttcc ataggctccg 1080
cccccctgac gagcatcaca aaaatcgacg ctcaagtcag aggtggcgaa acccgacagg 1140
actataaaga taccaggcgt ttccccctgg aagctccctc gtgcgctctc ctgttccgac 1200
cctgccgctt accggatacc tgtccgcctt tctcccttcg ggaagcgtgg cgctttctca 1260
tagctcacgc tgtaggtatc tcagttcggt gtaggtcgtt cgctccaagc tgggctgtgt 1320
gcacgaaccc cccgttcagc ccgaccgctg cgccttatcc ggtaactatc gtcttgagtc 1380
caacccggta agacacgact tatcgccact ggcagcagcc actggtaaca ggattagcag 1440
agcgaggtat gtaggcggtg ctacagagtt cttgaagtgg tggcctaact acggctacac 1500
tagaagaaca gtatttggta tctgcgctct gctgaagcca gttaccttcg gaaaaagagt 1560
tggtagctct tgatccggca aacaaaccac cgctggtagc ggtggttttt ttgtttgcaa 1620

-continued

```
gcagcagatt acgcgcagaa aaaaaggatc tcaagaagat cctttgatct tttctacggg   1680
gtctgacgct cagctagcgc tcagaagaac tcgtcaagaa ggcgatagaa ggcgatgcgc   1740
tgcgaatcgg gagcggcgat accgtaaagc acgaggaagc ggtcagccca ttcgccgcca   1800
agctcttcag caatatcacg ggtagccaac gctatgtcct gatagcggtc cgccacaccc   1860
agccggccac agtcgatgaa tccagaaaag cggccatttt ccaccatgat attcggcaag   1920
caggcatcgc catgagtcac gacgagatcc tcgccgtcgg gcatgcgcgc cttgagcctg   1980
gcgaacagtt cggctggcgc gagcccctga tgctcttcgt ccagatcatc ctgatcgaca   2040
agaccggctt ccatccgagt acgtgctcgc tcgatgcgat gtttcgcttg gtggtcgaat   2100
gggcaggtag ccggatcaag cgtatgcagc cgccgcattg catcagccat gatggatact   2160
ttctcggcag gagcaaggtg agatgacagg agatcctgcc ccggcacttc gcccaatagc   2220
agccagtccc ttcccgcttc agtgacaacg tcgagcacag ctgcgcaagg aacgcccgtc   2280
gtggccagcc acgatagccg cgctgcctcg tcctgcagtt cattcagggc accggacagg   2340
tcggtcttga caaaaagaac cgggcgcccc tgcgctgaca gccggaacac ggcggcatca   2400
gagcagccga ttgtctgttg tgcccagtca tagccgaata gcctctccac ccaagcggcc   2460
ggagaacctg cgtgcaatcc atcttgttca atcatgcgaa acgatcctca tcctgtctct   2520
tgatcagatc ttgatcccct gcgccatcag atccttggcg gcaagaaagc catccagttt   2580
actttgcagg gcttcccaac cttaccagag ggcgccccag ctggcaattc cggttcgctt   2640
gctgtccata aaaccgccca gtctagcaac tgttgggaag ggcgatcgtg taatacgact   2700
cactataggg cgaattggag ct                                            2722
```

<210> SEQ ID NO 18
<211> LENGTH: 2725
<212> TYPE: DNA
<213> ORGANISM: artificial sequence
<220> FEATURE:
<223> OTHER INFORMATION: Plasmid vector having a codon optimized rat GHRH sequence

<400> SEQUENCE: 18

```
ccaccgcggt ggcggccgtc cgccctcggc accatcctca cgacacccaa atatggcgac     60
gggtgaggaa tggtggggag ttatttttag agcggtgagg aaggtgggca ggcagcaggt    120
gttggcgctc taaaaataac tcccgggagt tatttttaga gcggaggaat ggtggacacc    180
caaatatggc gacggttcct cacccgtcgc catatttggg tgtccgccct cggccggggc    240
cgcattcctg gggggccgggc ggtgctcccg cccgcctcga taaaaggctc cggggccggc   300
ggcggcccac gagctacccg gaggagcggg aggcgccaag cggatcccaa ggcccaactc    360
cccgaaccac tcagggtcct gtggacagct cacctagctg ccatggccct gtgggtgttc    420
ttcgtgctgc tgaccctgac cagcggaagc cactgcagcc tgcctcccag ccctcccttc    480
agggtgcgcc ggcacgccga cgccatcttc accagcagct acaggaggat cctgggccag    540
ctgtacgcta ggaagctcct gcacgagatc atgaacaggc agcagggcga gaggaaccag    600
gagcagagga gcaggttcaa ctgataagct tatcggggtg gcatccctgt gacccctccc    660
cagtgcctct cctggccctg gaagttgcca ctccagtgcc caccagcctt gtcctaataa    720
aattaagttg catcattttg tctgactagg tgtccttcta taatattatg gggtggaggg    780
gggtggtatg gagcaagggg caagttggga agacaacctg tagggctcga ggggggggccc   840
ggtaccagct tttgttccct ttagtgaggg ttaatttcga gcttggtctt ccgcttcctc    900
```

-continued

```
gctcactgac tcgctgcgct cggtcgttcg gctgcggcga gcggtatcag ctcactcaaa    960

ggcggtaata cggttatcca cagaatcagg ggataacgca ggaaagaaca tgtgagcaaa   1020

aggccagcaa aaggccagga accgtaaaaa ggccgcgttg ctggcgtttt tccataggct   1080

ccgcccccct gacgagcatc acaaaaatcg acgctcaagt cagaggtggc gaaacccgac   1140

aggactataa agataccagg cgtttccccc tggaagctcc ctcgtgcgct ctcctgttcc   1200

gaccctgccg cttaccggat acctgtccgc ctttctccct tcgggaagcg tggcgctttc   1260

tcatagctca cgctgtaggt atctcagttc ggtgtaggtc gttcgctcca agctgggctg   1320

tgtgcacgaa ccccccgttc agcccgaccg ctgcgcctta tccggtaact atcgtcttga   1380

gtccaacccg gtaagacacg acttatcgcc actggcagca gccactggta acaggattag   1440

cagagcgagg tatgtaggcg gtgctacaga gttcttgaag tggtggccta actacggcta   1500

cactagaaga acagtatttg gtatctgcgc tctgctgaag ccagttacct tcggaaaaag   1560

agttggtagc tcttgatccg gcaaacaaac caccgctggt agcggtggtt tttttgtttg   1620

caagcagcag attacgcgca gaaaaaaagg atctcaagaa gatcctttga tcttttctac   1680

ggggtctgac gctcagctag cgctcagaag aactcgtcaa gaaggcgata gaaggcgatg   1740

cgctgcgaat cgggagcggc gataccgtaa agcacgagga agcggtcagc ccattcgccg   1800

ccaagctctt cagcaatatc acgggtagcc aacgctatgt cctgatagcg gtccgccaca   1860

cccagccggc cacagtcgat gaatccagaa aagcggccat tttccaccat gatattcggc   1920

aagcaggcat cgccatgagt cacgacgaga tcctcgccgt cgggcatgcg cgccttgagc   1980

ctggcgaaca gttcggctgg cgcgagcccc tgatgctctt cgtccagatc atcctgatcg   2040

acaagaccgg cttccatccg agtacgtgct cgctcgatgc gatgtttcgc ttggtggtcg   2100

aatgggcagg tagccggatc aagcgtatgc agccgccgca ttgcatcagc catgatggat   2160

actttctcgg caggagcaag gtgagatgac aggagatcct gccccggcac ttcgcccaat   2220

agcagccagt cccttcccgc ttcagtgaca acgtcgagca cagctgcgca aggaacgccc   2280

gtcgtggcca gccacgatag ccgcgctgcc tcgtcctgca gttcattcag ggcaccggac   2340

aggtcggtct tgacaaaaag aaccgggcgc ccctgcgctg acagccggaa cacggcggca   2400

tcagagcagc cgattgtctg ttgtgcccag tcatagccga atagcctctc cacccaagcg   2460

gccggagaac ctgcgtgcaa tccatcttgt tcaatcatgc gaaacgatcc tcatcctgtc   2520

tcttgatcag atcttgatcc cctgcgccat cagatccttg gcggcaagaa agccatccag   2580

tttactttgc agggcttccc aaccttacca gagggcgccc cagctggcaa ttccggttcg   2640

cttgctgtcc ataaaaccgc ccagtctagc aactgttggg aagggcgatc gtgtaatacg   2700

actcactata gggcgaattg gagct                                         2725
```

<210> SEQ ID NO 19
<211> LENGTH: 2716
<212> TYPE: DNA
<213> ORGANISM: artificial sequence
<220> FEATURE:
<223> OTHER INFORMATION: Plasmid vector having a codon optimized bovine GHRH sequence

<400> SEQUENCE: 19

```
ccaccgcggt ggcggccgtc cgccctcggc accatcctca cgacacccaa atatggcgac     60

gggtgaggaa tggtggggag ttatttttag agcggtgagg aaggtgggca ggcagcaggt    120

gttggcgctc taaaaataac tcccgggagt tatttttaga gcggaggaat ggtggacacc    180
```

-continued

```
caaatatggc gacggttcct cacccgtcgc catatttggg tgtccgccct cggccggggc    240
cgcattcctg gggccgggc ggtgctcccg cccgcctcga taaaaggctc cggggccggc     300
ggcggcccac gagctacccg gaggagcggg aggcgccaag cggatcccaa ggcccaactc    360
cccgaaccac tcagggtcct gtggacagct cacctagctg ccatggtgct gtgggtgttc    420
ttcctggtga ccctgaccct gagcagcggc tcccacggct ccctgccctc ccagcctctg    480
cgcatccctc gctacgccga cgccatcttc accaacagct accgcaaggt gctcggccag    540
ctcagcgccc gcaagctcct gcaggacatc atgaaccggc agcagggcga gcgcaaccag    600
gagcagggag cctgataagc ttatcggggt ggcatccctg tgacccctcc ccagtgcctc    660
tcctggccct ggaagttgcc actccagtgc ccaccagcct tgtcctaata aaattaagtt    720
gcatcatttt gtctgactag gtgtccttct ataatattat ggggtggagg ggggtggtat    780
ggagcaaggg gcaagttggg aagacaacct gtagggctcg aggggggccc cggtaccagc    840
ttttgttccc tttagtgagg gttaatttcg agcttggtct tccgcttcct cgctcactga    900
ctcgctgcgc tcggtcgttc ggctgcggcg agcggtatca gctcactcaa aggcggtaat    960
acggttatcc acagaatcag gggataacgc aggaaagaac atgtgagcaa aaggccagca   1020
aaaggccagg aaccgtaaaa aggccgcgtt gctggcgttt ttccataggc tccgcccccc   1080
tgacgagcat cacaaaaatc gacgctcaag tcagaggtgg cgaaacccga caggactata   1140
aagataccag gcgtttcccc ctggaagctc cctcgtgcgc tctcctgttc cgaccctgcc   1200
gcttaccgga tacctgtccg cctttctccc ttcgggaagc gtggcgcttt ctcatagctc   1260
acgctgtagg tatctcagtt cggtgtaggt cgttcgctcc aagctgggct gtgtgcacga   1320
accccccgtt cagcccgacc gctgcgcctt atccggtaac tatcgtcttg agtccaaccc   1380
ggtaagacac gacttatcgc cactggcagc agccactggt aacaggatta gcagagcgag   1440
gtatgtaggc ggtgctacag agttcttgaa gtggtggcct aactacggct acactagaag   1500
aacagtattt ggtatctgcg ctctgctgaa gccagttacc ttcggaaaaa gagttggtag   1560
ctcttgatcc ggcaaacaaa ccaccgctgg tagcggtggt ttttttgttt gcaagcagca   1620
gattacgcgc agaaaaaaag gatctcaaga agatcctttg atcttttcta cggggtctga   1680
cgctcagcta gcgctcagaa gaactcgtca agaaggcgat agaaggcgat gcgctgcgaa   1740
tcgggagcgg cgataccgta aagcacgagg aagcggtcag cccattcgcc gccaagctct   1800
tcagcaatat cacgggtagc caacgctatg tcctgatagc ggtccgccac acccagccgg   1860
ccacagtcga tgaatccaga aaagcggcca ttttccacca tgatattcgg caagcaggca   1920
tcgccatgag tcacgacgag atcctcgccg tcgggcatgc gcgccttgag cctggcgaac   1980
agttcggctg gcgcgagccc ctgatgctct tcgtccagat catcctgatc gacaagaccg   2040
gcttccatcc gagtacgtgc tcgctcgatg cgatgtttcg cttggtggtc gaatgggcag   2100
gtagccggat caagcgtatg cagccgccgc attgcatcag ccatgatgga tactttctcg   2160
gcaggagcaa ggtgagatga caggagatcc tgccccggca cttcgcccaa tagcagccag   2220
tcccttcccg cttcagtgac aacgtcgagc acagctgcgc aaggaacgcc cgtcgtggcc   2280
agccacgata gccgcgctgc ctcgtcctgc agttcattca gggcaccgga caggtcggtc   2340
ttgacaaaaa gaaccgggcg cccctgcgct gacagccgga acacggcggc atcagagcag   2400
ccgattgtct gttgtgccca gtcatagccg aatagcctct ccacccaagc ggccggagaa   2460
cctgcgtgca atccatcttg ttcaatcatg cgaaacgatc ctcatcctgt ctcttgatca   2520
gatcttgatc ccctgcgcca tcagatcctt ggcggcaaga aagccatcca gtttactttg   2580
```

-continued

```
cagggcttcc caaccttacc agagggcgcc ccagctggca attccggttc gcttgctgtc   2640

cataaaaccg cccagtctag caactgttgg gaagggcgat cgtgtaatac gactcactat   2700

agggcgaatt ggagct                                                   2716
```

<210> SEQ ID NO 20
<211> LENGTH: 2716
<212> TYPE: DNA
<213> ORGANISM: artificial sequence
<220> FEATURE:
<223> OTHER INFORMATION: Plasmid vector having a codon optimized ovine GHRH sequence

<400> SEQUENCE: 20

```
ccaccgcggt ggcggccgtc cgccctcggc accatcctca cgacacccaa atatggcgac     60

gggtgaggaa tggtggggag ttatttttag agcggtgagg aaggtgggca ggcagcaggt    120

gttggcgctc taaaaataac tcccgggagt tatttttaga gcggaggaat ggtggacacc    180

caaatatggc gacggttcct cacccgtcgc catatttggg tgtccgccct cggccggggc    240

cgcattcctg ggggccgggc ggtgctcccg cccgcctcga taaaaggctc cggggccggc    300

ggcggcccac gagctacccg gaggagcggg aggcgccaag cggatcccaa ggcccaactc    360

cccgaaccac tcagggtcct gtggacagct cacctagctg ccatggtgct gtgggtgttc    420

ttcctggtga ccctgaccct gagcagcgga agccacggca gcctgcccag ccagcccctg    480

aggatcccta ggtacgccga cgccatcttc accaacagct acaggaagat cctgggccag    540

ctgagcgcta ggaagctcct gcaggacatc atgaacaggc agcagggcga gaggaaccag    600

gagcagggcg cctgataagc ttatcggggt ggcatccctg tgacccctcc ccagtgcctc    660

tcctggccct ggaagttgcc actccagtgc ccaccagcct tgtcctaata aaattaagtt    720

gcatcatttt gtctgactag gtgtccttct ataatattat ggggtggagg ggggtggtat    780

ggagcaaggg gcaagttggg aagacaacct gtagggctcg agggggggcc cggtaccagc    840

ttttgttccc tttagtgagg gttaatttcg agcttggtct tccgcttcct cgctcactga    900

ctcgctgcgc tcggtcgttc ggctgcggcg agcggtatca gctcactcaa aggcggtaat    960

acggttatcc acagaatcag gggataacgc aggaaagaac atgtgagcaa aaggccagca   1020

aaaggccagg aaccgtaaaa aggccgcgtt gctggcgttt ttccataggc tccgcccccc   1080

tgacgagcat cacaaaaatc gacgctcaag tcagaggtgg cgaaacccga caggactata   1140

aagataccag gcgtttcccc ctggaagctc cctcgtgcgc tctcctgttc cgaccctgcc   1200

gcttaccgga tacctgtccg cctttctccc ttcgggaagc gtggcgcttt ctcatagctc   1260

acgctgtagg tatctcagtt cggtgtaggt cgttcgctcc aagctgggct gtgtgcacga   1320

accccccgtt cagcccgacc gctgcgcctt atccggtaac tatcgtcttg agtccaaccc   1380

ggtaagacac gacttatcgc cactggcagc agccactggt aacaggatta gcagagcgag   1440

gtatgtaggc ggtgctacag agttcttgaa gtggtggcct aactacggct acactagaag   1500

aacagtattt ggtatctgcg ctctgctgaa gccagttacc ttcggaaaaa gagttggtag   1560

ctcttgatcc ggcaaacaaa ccaccgctgg tagcggtggt ttttttgttt gcaagcagca   1620

gattacgcgc agaaaaaaag gatctcaaga agatcctttg atcttttcta cggggtctga   1680

cgctcagcta gcgctcagaa gaactcgtca agaaggcgat agaaggcgat gcgctgcgaa   1740

tcgggagcgg cgataccgta aagcacgagg aagcggtcag cccattcgcc gccaagctct   1800

tcagcaatat cacgggtagc caacgctatg tcctgatagc ggtccgccac acccagccgg   1860
```

-continued

```
ccacagtcga tgaatccaga aaagcggcca ttttccacca tgatattcgg caagcaggca   1920

tcgccatgag tcacgacgag atcctcgccg tcgggcatgc gcgccttgag cctggcgaac   1980

agttcggctg gcgcgagccc ctgatgctct tcgtccagat catcctgatc gacaagaccg   2040

gcttccatcc gagtacgtgc tcgctcgatg cgatgtttcg cttggtggtc gaatgggcag   2100

gtagccggat caagcgtatg cagccgccgc attgcatcag ccatgatgga tactttctcg   2160

gcaggagcaa ggtgagatga caggagatcc tgccccggca cttcgcccaa tagcagccag   2220

tcccttcccg cttcagtgac aacgtcgagc acagctgcgc aaggaacgcc cgtcgtggcc   2280

agccacgata gccgcgctgc ctcgtcctgc agttcattca gggcaccgga caggtcggtc   2340

ttgacaaaaa gaaccgggcg cccctgcgct gacagccgga acacggcggc atcagagcag   2400

ccgattgtct gttgtgccca gtcatagccg aatagcctct ccacccaagc ggccggagaa   2460

cctgcgtgca atccatcttg ttcaatcatg cgaaacgatc ctcatcctgt ctcttgatca   2520

gatcttgatc ccctgcgcca tcagatcctt ggcggcaaga aagccatcca gtttactttg   2580

cagggcttcc caaccttacc agagggcgcc ccagctggca attccggttc gcttgctgtc   2640

cataaaaccg cccagtctag caactgttgg gaagggcgat cgtgtaatac gactcactat   2700

agggcgaatt ggagct                                                   2716
```

<210> SEQ ID NO 21
<211> LENGTH: 2725
<212> TYPE: DNA
<213> ORGANISM: artificial sequence
<220> FEATURE:
<223> OTHER INFORMATION: Plasmid vector having a codon optimized chicken GHRH sequence

<400> SEQUENCE: 21

```
ccaccgcggt ggcggccgtc cgccctcggc accatcctca cgacacccaa atatggcgac     60

gggtgaggaa tggtggggag ttatttttag agcggtgagg aaggtgggca ggcagcaggt    120

gttggcgctc taaaaataac tcccgggagt tatttttaga gcggaggaat ggtggacacc    180

caaatatggc gacggttcct cacccgtcgc catatttggg tgtccgccct cggccggggc    240

cgcattcctg gggccgggc ggtgctcccg cccgcctcga taaaaggctc cggggccggc    300

ggcggcccac gagctacccg gaggagcggg aggcgccaag cggatcccaa ggcccaactc    360

cccgaaccac tcagggtcct gtggacagct cacctagctg ccatggccct gtgggtgttc    420

tttgtgctgc tgaccctgac ctccggaagc cactgcagcc tgccacccag cccacccttc    480

cgcgtcaggc gccacgccga cggcatcttc agcaaggcct accgcaagct cctgggccag    540

ctgagcgcac gcaactacct gcacagcctg atggccaagc gcgtgggcag cggactggga    600

gacgaggccg agcccctgag ctgataagct tatcggggtg gcatccctgt gacccctccc    660

cagtgcctct cctggccctg gaagttgcca ctccagtgcc caccagcctt gtcctaataa    720

aattaagttg catcattttg tctgactagg tgtccttcta taatattatg gggtggaggg    780

gggtggtatg gagcaagggg caagttggga agacaacctg tagggctcga ggggggggcc    840

ggtaccagct tttgttccct ttagtgaggg ttaatttcga gcttggtctt ccgcttcctc    900

gctcactgac tcgctgcgct cggtcgttcg gctgcggcga gcggtatcag ctcactcaaa    960

ggcggtaata cggttatcca cagaatcagg ggataacgca ggaaagaaca tgtgagcaaa   1020

aggccagcaa aaggccagga accgtaaaaa ggccgcgttg ctggcgtttt tccataggct   1080

ccgcccccct gacgagcatc acaaaaatcg acgctcaagt cagaggtggc gaaacccgac   1140
```

-continued

```
aggactataa agataccagg cgtttccccc tggaagctcc ctcgtgcgct ctcctgttcc   1200
gaccctgccg cttaccggat acctgtccgc ctttctccct tcgggaagcg tggcgctttc   1260
tcatagctca cgctgtaggt atctcagttc ggtgtaggtc gttcgctcca agctgggctg   1320
tgtgcacgaa ccccccgttc agcccgaccg ctgcgcctta tccggtaact atcgtcttga   1380
gtccaacccg gtaagacacg acttatcgcc actggcagca gccactggta acaggattag   1440
cagagcgagg tatgtaggcg gtgctacaga gttcttgaag tggtggccta actacggcta   1500
cactagaaga acagtatttg gtatctgcgc tctgctgaag ccagttacct tcggaaaaag   1560
agttggtagc tcttgatccg gcaaacaaac caccgctggt agcggtggtt tttttgtttg   1620
caagcagcag attacgcgca gaaaaaaagg atctcaagaa gatcctttga tcttttctac   1680
ggggtctgac gctcagctag cgctcagaag aactcgtcaa gaaggcgata gaaggcgatg   1740
cgctgcgaat cgggagcggc gataccgtaa agcacgagga agcggtcagc ccattcgccg   1800
ccaagctctt cagcaatatc acgggtagcc aacgctatgt cctgatagcg gtccgccaca   1860
cccagccggc cacagtcgat gaatccagaa aagcggccat tttccaccat gatattcggc   1920
aagcaggcat cgccatgagt cacgacgaga tcctcgccgt cgggcatgcg cgccttgagc   1980
ctggcgaaca gttcggctgg cgcgagcccc tgatgctctt cgtccagatc atcctgatcg   2040
acaagaccgg cttccatccg agtacgtgct cgctcgatgc gatgtttcgc ttggtggtcg   2100
aatgggcagg tagccggatc aagcgtatgc agccgccgca ttgcatcagc catgatggat   2160
actttctcgg caggagcaag gtgagatgac aggagatcct gccccggcac ttcgcccaat   2220
agcagccagt cccttcccgc ttcagtgaca acgtcgagca cagctgcgca aggaacgccc   2280
gtcgtggcca gccacgatag ccgcgctgcc tcgtcctgca gttcattcag ggcaccggac   2340
aggtcggtct tgacaaaaag aaccgggcgc ccctgcgctg acagccggaa cacggcggca   2400
tcagagcagc cgattgtctg ttgtgcccag tcatagccga atagcctctc cacccaagcg   2460
gccggagaac ctgcgtgcaa tccatcttgt tcaatcatgc gaaacgatcc tcatcctgtc   2520
tcttgatcag atcttgatcc cctgcgccat cagatccttg gcggcaagaa agccatccag   2580
tttactttgc agggcttccc aaccttacca gagggcgccc cagctggcaa ttccggttcg   2640
cttgctgtcc ataaaaccgc ccagtctagc aactgttggg aagggcgatc gtgtaatacg   2700
actcactata gggcgaattg gagct                                         2725
```